United States Patent
Ciliberti et al.

(10) Patent No.: US 12,159,646 B2
(45) Date of Patent: Dec. 3, 2024

(54) COUGH DETECTION SYSTEM

(71) Applicant: Express Scripts Strategic Development, Inc., St. Louis, MO (US)

(72) Inventors: John Ciliberti, Sparta, NJ (US); Anatoly Zheleznyak, Old Bridge, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 946 days.

(21) Appl. No.: 17/188,462

(22) Filed: Mar. 1, 2021

(65) Prior Publication Data

US 2022/0277764 A1    Sep. 1, 2022

(51) Int. Cl.

| | |
|---|---|
| G10L 25/66 | (2013.01) |
| A61B 5/08 | (2006.01) |
| G06N 3/08 | (2023.01) |
| G10L 15/06 | (2013.01) |
| G16H 10/20 | (2018.01) |
| G16H 10/60 | (2018.01) |
| G16H 50/20 | (2018.01) |

(52) U.S. Cl.
CPC ............ *G10L 25/66* (2013.01); *A61B 5/08* (2013.01); *A61B 5/0823* (2013.01); *G06N 3/08* (2013.01); *G10L 15/063* (2013.01); *G16H 10/20* (2018.01); *G16H 10/60* (2018.01); *G16H 50/20* (2018.01); *G10L 2015/0635* (2013.01)

(58) Field of Classification Search
None
See application file for complete search history.

(56) References Cited

U.S. PATENT DOCUMENTS

| | | | |
|---|---|---|---|
| 6,436,057 B1 | 8/2002 | Goldsmith | |
| 9,526,458 B2 | 12/2016 | Macauslan | |
| 10,258,304 B1* | 4/2019 | Kiraly | ............ A61B 5/08 |
| 10,353,937 B2* | 7/2019 | Moeller-Bertram | .... G06F 15/76 |

(Continued)

OTHER PUBLICATIONS

A. Hadjahmadi, M. H. Ziyaaddini and M. Mehdi Omid, "Using End-to-End Deep Neural Networks for Diagnosing Drug Addiction from Speech Signals," 2020 6th Iranian Conference on Signal Processing and Intelligent Systems (ICSPIS), Mashhad, Iran, 2020, pp. 1-6 (Year: 2020).*

(Continued)

*Primary Examiner* — Benjamin S Melhus
*Assistant Examiner* — Samuel C Kim
(74) *Attorney, Agent, or Firm* — Miller Johnson

(57) ABSTRACT

Methods and systems for a cough detection system are provided. The methods and systems include operations comprising: receiving an utterance comprising a cough from a user; determining one or more environmental factors, one or more health related factors, or both associated with the user; processing the utterance with a machine learning technique to generate an illness prediction, the machine learning technique being trained to establish a relationship between a plurality of training cough utterances and a plurality of illnesses corresponding to the plurality of training cough utterances; applying a weight to the illness prediction based on the one or more environmental factors, health related factors, or both associated with the user; and triggering an alert representing the illness prediction based on the weighted illness prediction.

19 Claims, 13 Drawing Sheets

(56) References Cited

U.S. PATENT DOCUMENTS

| | | | |
|---|---|---|---|
| 10,485,449 B2 | 11/2019 | Macauslan | |
| 10,896,763 B2 | 1/2021 | Kempanna | |
| 10,936,936 B2 | 3/2021 | Hill | |
| 10,977,522 B2* | 4/2021 | Anushiravani | G06V 10/82 |
| 11,004,449 B2 | 5/2021 | Bender | |
| 11,504,011 B1* | 11/2022 | Jain | G06N 5/04 |
| 11,589,219 B2* | 2/2023 | Rivers | H04W 12/69 |
| 2002/0035486 A1* | 3/2002 | Huyn | G09B 7/02 |
| | | | 705/3 |
| 2005/0228242 A1* | 10/2005 | Kawamura | A61B 5/7275 |
| | | | 128/920 |
| 2012/0071777 A1* | 3/2012 | MacAuslan | A61B 5/7282 |
| | | | 600/529 |
| 2012/0116186 A1 | 5/2012 | Shrivastav | |
| 2013/0158368 A1* | 6/2013 | Pacione | A61B 5/318 |
| | | | 600/595 |
| 2014/0336537 A1 | 11/2014 | Patel | |
| 2015/0019256 A1* | 1/2015 | Doyle | G16H 40/67 |
| | | | 705/3 |
| 2015/0196269 A1 | 7/2015 | Rajan | |
| 2015/0245788 A1 | 9/2015 | Schmidt | |
| 2018/0214061 A1 | 8/2018 | Knoth | |
| 2020/0098366 A1 | 3/2020 | Chakraborty | |
| 2020/0125928 A1 | 4/2020 | Doyle | |
| 2020/0312298 A1 | 10/2020 | Bui | |
| 2021/0007645 A1* | 1/2021 | Nakatsugawa | A61B 5/486 |
| 2021/0019611 A1 | 1/2021 | Kothuvatiparambil | |
| 2021/0027893 A1* | 1/2021 | Nematihosseinabadi | |
| | | | A61B 5/1112 |
| 2021/0052231 A1* | 2/2021 | Naga Sripada | A61B 5/746 |
| 2021/0145306 A1* | 5/2021 | Karankevich | A61B 5/7246 |
| 2021/0219893 A1 | 7/2021 | Luz | |
| 2021/0386320 A1* | 12/2021 | Lesso | A61B 5/0803 |

OTHER PUBLICATIONS

Chu, Artificial intelligence model detects asymptomatic Covid-19 infections through cellphone-recorded coughs, MIT News, https://news.mit.edu/2020/covid-19-cough-cellphone-detection-1029, accessed as early as Nov. 1, 2020.

Gizmodo, Researchers Built an App That Aims to Detect Covid-19 by Listening to Your Coughs, https://gizmodo.com/researchers-built-an-app-that-aims-to-detect-covid-19-b-1842613139, accessed as early as Nov. 1, 2020.

* cited by examiner

600

Welcome Jon!!

March 14 — 620

Please respond truthfully below:

610
Have you or your family experienced health related symptoms like fatigue or fever in the past 24 hours?

| Yes |
| No |

Have you had contact with someone who tested positive for the infection?

| Yes |
| No |

Have you left the country in the past 72 hours?

| Yes |
| No |

630
Have you been tested for infection in the past week?

| Yes |
| No |

640
Please record a cough

642
Record Cough

*FIG. 6*

COUGH DETECTION SYSTEM

BACKGROUND

Users are increasingly using websites via the Internet to access information and perform transactions. For example, users can access websites to complete surveys, including questionnaires relating to health information that are used to control social spread of infection among individuals within a community.

BRIEF DESCRIPTION OF THE DRAWINGS

FIG. 6 illustrates an example questionnaire that can be deployed within the cough detection system, according to some embodiments.

DETAILED DESCRIPTION

Figure 1:
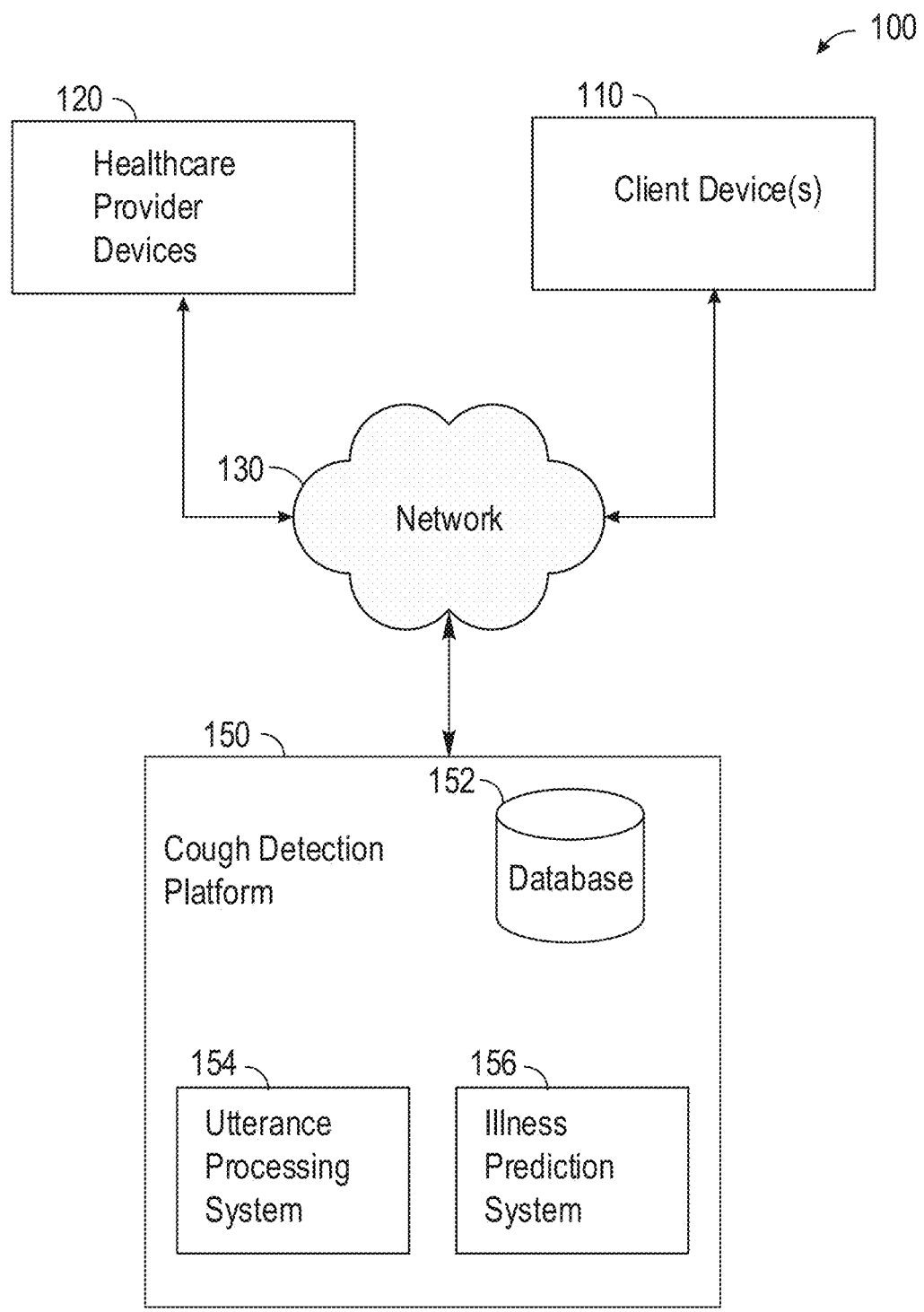
FIG. 1 is a block diagram of an example cough detection system, according to some embodiments.

Example methods and systems for a cough detection system are provided. In the following description, for purposes of explanation, numerous specific details are set forth in order to provide a thorough understanding of example embodiments. It will be evident, however, to one of ordinary skill in the art that embodiments of the invention may be practiced without these specific details.

As the world begins to return to worksites and children are being sent back to school, digital applications that require people (employees, students, parents, etc.) to complete daily attestations of their personal health (symptoms, temperature, etc.), social behaviors (social distancing precautions, contact with people who are positive with an illness, such as the novel coronavirus (COVID-19 or COVID), etc.) and whereabouts (travel outside of the country, etc.) are becoming more common. For example, such attestations can be submitted as responses to questionnaires or surveys. Digital applications are loaded into machines that become dedicated machines when operating the digital application.

Users can access an online questionnaire to answer various social and health related questions. These questionnaires are used to control social spread of infection among individuals. As such, maintaining accuracy and truthfulness in the responses to the questionnaires is of utmost importance. Some questions of these questionnaires confirm that a user is infected by a particular disease or illness based on responses to specific health related questions (e.g., whether the user experienced a fever in the past few days). However, certain diseases can continue to be spread by an infected individual who presents with no symptoms at all (e.g., users can be asymptomatic). Such users would respond negatively to the specific health related questions and would not be identified by the questionnaires as being infected by an illness at all. This calls into question the accuracy and the overall reliability of the questionnaires.

The disclosed embodiments provide systems and methods to detect an illness based on an utterance comprising a cough by applying a trained machine learning model to the utterance. The systems and methods can then automatically notify the user who coughed about the possibility of infection and/or can notify other users who were possibly exposed to the illness by virtue of being in a vicinity of or proximity to the user who coughed. Specifically, the disclosed embodiments receive an utterance comprising a cough from a user (e.g., as part of completing an attestation questionnaire or passively from a microphone installed in a room) and determine one or more environmental factors and/or one or more health related factors associated with the user. The disclosed embodiments process the utterance with a machine learning technique to generate an illness prediction. The machine learning technique is trained to establish a relationship between a plurality of training cough utterances and a plurality of illnesses corresponding to the plurality of training cough utterances. The disclosed embodiments apply a weight to the illness prediction based on the one or more environmental and/or health related factors associated with the user and trigger an alert representing the illness prediction based on the weighted illness prediction.

In this way, by collecting utterances as part of questionnaires and determining whether the utterances are indicative of a possible infection, the accuracy and overall reliability of the questionnaires is enhanced by the disclosed embodiments. This improves the ability for employers, communities and schools to control the social spread of infection among individuals.

In one example, the disclosed embodiments, can collect utterances in a public space passively and notify users who are currently in, who have been, or who enter the public space of possible exposure to the illness associated with the cough. To enhance privacy, the disclosed embodiments request or allow users who enter the public space to opt into receiving exposure notifications of the illnesses. Locations of client devices of users who decide to opt into receiving such exposure notifications are tracked and used to determine whether to send the exposure notifications based on detection of a cough (indicative of an illness) in the vicinity of the locations at a current time or at an earlier point in time.

In another example, a user's client device can be used to access an interactive voice response system. The interactive voice response system can collect various health related information from the user and can access prior health information for the user. For example, the voice response system can be accessed by the user to re-fill a prescription. During access to the interactive voice response system, an utterance that includes a cough from the user can be detected. The interactive voice response system processes the utterance with a trained machine learning model. In response to determining that the output of the trained machine learning model indicates that the utterance corresponds to an illness prediction, the interactive voice response system can notify the user to get tested for the illness and/or can notify a health care professional to contact the user to perform further analysis and help the user.

In another example, a client device can be used to request a test to verify whether a user is infected by an illness. The client device can communicate with a server to request that a test be conducted. The server can collect an utterance from the user that includes a cough. The server can then process the utterance with a trained machine learning model. In response to determining that the output of the trained machine learning model indicates that the utterance corresponds to an illness prediction, the server selects a particular testing kit of a plurality of testing kits. In an implementation, each testing kit for detecting whether a user is infected by an illness can be associated with a different level of accuracy and can take different amounts of time to return results. If the server determines that the utterance does not correspond to an illness prediction (e.g., the probability or likelihood or weight associated with the illness prediction is below a threshold), the server selects a first testing kit that has a lower level of accuracy than a second testing kit and that provides results faster than the second testing kit. If the server determines that the utterance corresponds to an illness prediction (e.g., the probability or likelihood or weight associated with the illness prediction is above a threshold), the server selects the second testing kit with the higher level of accuracy. The server then transmits an alert to the client device that includes an indication of the selected testing kit the user is authorized to use to conduct the test for the illness.

In another example, the disclosed embodiments analyze changes to a user's voice over time. For example, the disclosed embodiments can collect samples of the user's voice each time the user re-fills a prescription (e.g., a prescription for an opioid). Based on changes to the user's voice, the disclosed embodiments can detect an addiction to the opioid. Specifically, the voice changes together with the type of prescription can be processed by a trained machine learning model. The machine learning model can be trained to establish a relationship between a plurality of training voice changes and prescription types and corresponding addiction classifications. If the machine learning model indicates the likelihood of an addiction, the disclosed embodiments can prevent the prescription from being re-filled and/or can contact a health care professional for follow up with the user.

FIG. 1 is a block diagram showing an example cough detection system 100 according to various exemplary embodiments. The cough detection system 100 includes one or more client devices 110, one or more healthcare provider devices 120, and a cough detection platform 150 that are communicatively coupled over a network 130 (e.g., Internet, telephony network).

As used herein, the term "client device" may refer to any machine that interfaces to a communications network (such as network 130) to access the cough detection platform 150. The client device 110 may be, but is not limited to, a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, or other communication device that a user may use to access a network, a dedicated application, or the cough detection platform 150. In an example embodiment, the use of client devices can provide a specialized pandemic disease detection system.

In some cases, the cough detection platform 150 is accessible over a global communication system, e.g., the Internet or world wide web. In such instances, the cough detection platform 150 hosts a website that is accessible to the client devices 110. Upon accessing the website, the client devices 110 provide secure login credentials, which are used to access a profile associated with the login credentials. One or more user interfaces associated with the cough detection platform 150 are provided over the Internet via the website to the client devices 110 (e.g., the user interfaces discussed in connection with FIGS. 6, 9 and 10).

Healthcare provider devices 120 can include the same or similar functionality as client devices 110 for accessing the cough detection platform 150. In some cases, the healthcare provider devices 120 are used by "internal" users. Internal users are personnel, such as physicians, clinicians, healthcare providers, health-related coaches or the like that are associated with or employed by an organization that provides the cough detection platform 150. In some cases, the healthcare provider devices 120 are used by "external" users. External users are personnel, such as physicians, clinicians, and health-related coaches that are associated with or employed by a different (external) organization than that which provides the cough detection platform 150.

The healthcare provider devices 120, when used by internal or external users, to access the cough detection platform 150 can view many records associated with many different patients (or users associated with client devices 110). Different levels of authorization can be associated with different internal and different external users to control which records the internal and external users have access. In some instances, only records associated with those patients to which a given internal or external user is referred (e.g., as a result of a positive illness prediction made by the illness prediction system 156 for a given user or patient), are made accessible and available to the given internal or external user device. Sometimes, a first internal or external user can refer a patient or records associated with the patient to a second internal or external user. In such circumstances, the second internal or external user becomes automatically authorized to access and view the patient's records that were referred by the first internal or external user. In an example embodiment, a referral flag can be set in a patient record in the database at the cough detection platform 150 in response to the illness prediction system 156 predicting an illness of the user based on detecting an utterance comprising a cough of the user and/or in response to determining that the user has been exposed to another person who has been predicted to have an illness by the illness prediction system 156. The referral flag provides authorization to a user of the healthcare provider devices 120 to view patient records and contact a patient (e.g., to discuss a possible infection or an illness or an addiction detected by the cough detection platform 150).

The network 130 may include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The healthcare provider devices 120 can be used to access pharmacy claims, medical data (e.g., medical information 230 stored in database 152), laboratory data and the like for one or more patients that the healthcare provider devices 120 are authorized to view. This patient information can be maintained in a database 152 by the cough detection platform 150 or in a third-party database accessible to the cough detection platform 150 and/or the healthcare provider devices 120.

In some embodiments, the client devices 110 and the cough detection platform 150 can be communicatively coupled via an audio call (e.g., VoIP, Public Switched Telephone Network, cellular communication network, etc.) or via electronic messages (e.g., online chat, instant messaging, text messaging, email, and the like). While FIG. 1 illustrates a single client device 110 and a single healthcare provider device 120, it is understood that a plurality of such devices can be included in the system 100 in other embodiments. As used herein, the term "client device" may refer to any machine that interfaces to a communications network (such as network 130) to obtain resources from one or more server systems or other client devices.

The cough detection platform 150 can be a human agent or an automated agent, e.g., on behalf of an organization. The automated agent can be associated with a medical group that includes the member. The automated agent can be an interactive voice response (IVR), a virtual online assistant, or a chatbot provided on a website. During a communication session between the user and the agent, the cough detection platform 150 identifies the member using initial context data (e.g., the phone number the member is calling from, the website login information inputted, automatic number identification (ANI), etc.) and retrieves the data on the member (e.g., member account information, name, address, insurance information, information on spouse and dependents, etc.) to be presented on the client device 110.

In some embodiments, the cough detection platform includes an utterance processing system 154 and an illness prediction system 156. The utterance processing system 154 is configured to continuously or periodically analyze utterances received from one or more microphones installed in one or more public spaces. In some implementations, the utterance processing system 154 is configured to continuously or periodically analyze utterances captured and received from one or more client devices 110. For example, the utterances can be captured and received during an IVR session between the client device 110 and the cough detection platform 150. In another example, the utterances can be captured when the client device 110 completes an illness questionnaire, survey or attestation and records the utterance as part of completing the illness questionnaire, survey or attestation.

The utterance processing system 154 processes the utterance to detect various information associated with an environment in which the utterance was captured. For example, the utterance processing system 154 can measure a level of ambient noise or can detect certain sounds (e.g., birds chirping) to determine that the utterance was captured outdoors in an outside public space rather than indoors. As another example, the utterance processing system 154 can determine whether certain characteristics of the utterance are indicative of a user speaking the utterance while wearing a mask. The utterance processing system 154 can also receive GPS or location information from the client device 110 from which the utterance was received or from a microphone that captured the utterance and can associate the location information with the utterance. The utterance processing system 154 determines that at least a portion of the utterance includes a cough. For example, the utterance processing system 154 can compare sound characteristics (e.g., frequency, duration and pitch) or apply known techniques to determine that a portion of the utterance includes a cough. In response, the utterance processing system 154 generates a sound clip (e.g., a 1 or 2 second sound clip) that includes only the portion of the utterance that includes the cough. The utterance processing system 154 associates the sound clip that includes the cough with the various information that has been determined (e.g., information indicating whether the utterance was received from indoors or outdoors, location information, and/or whether a mask was worn when the utterance was captured).

The utterance processing system 154 provides the sound clip that includes the utterance to the illness prediction system 156. The illness prediction system 156 implements a classifier or machine learning model (e.g., a neural network) that is trained to predict an illness based on the sound clip that includes a cough. Specifically, the illness prediction system 156 can generate features based on the sound clip. The illness prediction system 156 predicts or classifies the features of the sound clip with one or more illnesses. In an embodiment, the illness prediction system 156 provides a set of illnesses with their likelihoods or probabilities of matching the cough in the sound clip. In some cases, the illness prediction system 156 determines that the features of the sound clip are not indicative of an illness and, in such cases, outputs an illness prediction indicating that the cough does not match any known illness.

As explained in more detail in connection with FIG. 3, the illness prediction system 156 is trained based on training utterances comprising coughs and their corresponding ground-truth illnesses or lack thereof. The illness prediction system 156 is trained to predict whether features of a cough in a given sound clip correspond to one or more illnesses. For example, the illness prediction system 156 generates a prediction or set of likelihoods of each illness as corresponding to a given training sound clip that includes a cough. The illness prediction system 156 then compares the generated predictions with the known or ground-truth illnesses that correspond to the cough. The illness prediction system 156 computes a deviation based on the comparison and parameters of the illness prediction system 156 are updated based on the computed deviation. After processing a certain quantity or batch of training data or when a stopping criterion is met, the machine learning model implemented by the illness prediction system 156 is output as a trained machine learning model that can classify a cough with a certain likelihood as corresponding to one or more illnesses (e.g., COVID-19 or COPD). The classification is used as an illness prediction based on receipt of a new cough. Namely, the machine learning model of the illness prediction system 156 can be applied to a new sound clip that includes a cough to provide an illness prediction (e.g., a likelihood that the cough corresponds to one or more illnesses).

The output of the illness prediction system 156 that includes the illness prediction is then weighted based on additional information (e.g., environmental factors or health related factors) associated with the sound clip. The weighted illness prediction is then used to trigger an alert. For example, the weight associated with the illness prediction can be increased (e.g., to associate a higher likelihood of the accuracy of the illness prediction) if the additional information includes responses to a questionnaire indicating that the user from whom the utterance was received has recently traveled in the past week, has had a fever in the past week, experiences fatigue, and/or has been around another person infected with the same illness. The weight associated with the illness prediction can be decreased (e.g., to associate a lower likelihood of the accuracy of the illness prediction) if the additional information indicates that the cough was received from a user wearing mask. The weight associated with the illness prediction can be increased (e.g., to associate a higher likelihood of the accuracy of the illness prediction) if the additional information indicates that spectral density or intensity of the utterance that included the cough exceeds a specified threshold. For example, if the cough was received from a child a lower weight can be assigned to the prediction than if the cough was received from an adult.

In some embodiments, if the weighted illness prediction exceeds a specified threshold (e.g., the weighted predicted illness probability is greater than 60%), the cough detection platform 150 generates an alert to a user of the client device 110 indicating that the utterance that includes the cough is likely indicative of an illness (e.g., COVID-19). The alert can instruct the user to obtain a test kit or visit a testing site to verify whether the user actually has been infected by the illness. The results of the test can be received by the cough detection platform 150 and used to update a patient record for the user and/or to update the parameters of the trained illness prediction system 156. In some cases, the alert can be used to inform the user that the user is not authorized to enter or access a given public space due to the possible infection. Namely, the cough detection platform 150 can be used as a prescreening tool to allow or deny access to users to a certain protected space by having the users cough and determining the likelihood that the cough corresponds to a particular illness.

In some embodiments, the user of a client device 110 can request a specific testing kit to conduct a test to verify if the user has a particular illness. The cough detection platform 150 can request that the user provide an utterance that includes a cough. The cough detection platform 150 generates a likelihood or probability that the cough is associated with or corresponds to the illness, such as by applying a trained machine learning model to the cough to generate the illness prediction. The cough detection platform 150 can compare the illness prediction to a specified threshold. In response to determining that the illness prediction exceeds the specified threshold, the cough detection platform 150 selects a first type of testing kit to verify if the user has the particular illness. In response to determining that the illness prediction fails to exceed the specified threshold, the cough detection platform 150 selects a second type of testing kit to verify if the user has the particular illness. The second type of testing kit can generate results faster than the first type of testing kit but may generate such results with less accuracy than the first type of testing kit. The cough detection platform 150 may indicate to the user which type of testing kit the user is authorized to use to conduct the test to verify if the user is infected by the illness and can allow the user to order the selected testing kit. In this way, the cough detection platform 150 can control the type of testing kits and the level of accuracy of the tests performed on different users based on an analysis of whether their coughs likely or have a high probability of corresponding to a particular illness. In some cases, if the cough is indicative of or has a high likelihood of corresponding to the illness, the cough detection platform 150 prevents the user from conducting a test with the second testing kit that has the lower level of accuracy than the first testing kit.

In some embodiments, the alert is a flag value added to a patient record that includes various data inputs related to the user. The flag value can indicate the location where the user was when the utterance was detected. The patent record can be part of a relational database.

In some embodiments, the cough detection platform 150 determines that the utterance was received from a microphone installed in a public space (e.g., a park or a conference room). In such cases, the cough detection platform 150 identifies a list of users of client devices 110 that opted in or selected an option to receive illness exposure notifications. In response to determining that the weighted illness prediction exceeds the specified threshold (indicating that there is a high likelihood that the cough was received from a user infected by an illness), the cough detection platform 150 identifies a list of client devices 110 to alert about a possible exposure. To do so, the cough detection platform 150 applies one or more environmental factors associated with the microphone to generate a list of infection regions. Each infection region is associated with a different likelihood of infection.

In one example, the cough detection platform 150 generates a first ellipsoid or circle around the microphone that received the utterance that included the cough. The first ellipsoid or circle can include a first diameter or be of a first size based on its proximity to the microphone that received the utterance that included the cough or its proximity to the user from whom the utterance with the cough was received. The cough detection platform 150 can adjust the diameter or first size based on whether the additional information associated with the utterance indicates that the utterance was received indoors or outdoors. For example, the diameter or the first size can be a first amount that is smaller than a second amount if the additional information indicates that the utterance was received in an outdoor environment. The diameter or the first size can be a second amount that is larger than the first amount if the additional information indicates that the utterance was received in an indoor environment. In another example, the cough detection platform 150 can adjust the diameter or first size based on whether the additional information associated with the utterance indicates that the utterance was received from a user wearing a mask or not.

For example, the diameter or the first size can be a first amount that is smaller than a second amount if the additional information indicates that the user was wearing a mask. The diameter or the first size can be a second amount that is larger than the first amount if the additional information indicates that the user was not wearing a mask. The diameter or first size of the circle or ellipsoid can dynamically be shrunk or reduced in size over time. Namely, at a first point in time, the diameter or first size of the circle or ellipsoid can be a first amount and at a later second point in time (e.g., 10 minutes later), the diameter or first size of the circle or ellipsoid can be reduced to a second size. In some embodiments, the diameter or first size of the circle or ellipsoid can be increased or decreased based on a measure of humidity in the area in which the microphone is installed. For example, the diameter or first size can be proportionally increased or decreased by the level of humidity in the area.

The cough detection platform 150 can generate a second ellipsoid or circle around the first ellipsoid or circle. The second ellipsoid or circle can include a second diameter or be of a second size based on its proximity to the microphone that received the utterance that included the cough or the user from whom the utterance with the cough was received. The second diameter or second size of the second ellipsoid or circle can be maintained to be greater than the first diameter or first size of the first ellipsoid or circle. The cough detection platform 150 can adjust the diameter or second size of the second ellipsoid or circle in a similar manner as the first ellipsoid or circle (e.g., based on passage of time, based on whether the additional information associated with the utterance indicates that the utterance was received indoors or outdoors, and/or based on whether the additional information associated with the utterance indicates that the utterance was received from a user wearing a mask or not).

The cough detection platform 150 associates different weights for the illness prediction with each region encapsulated by or included within the first/second ellipsoids or circles. In an example, the cough detection platform 150 determines that a first client device 110 was located within a region covered by the first ellipsoid or circle when the utterance that includes the cough was received. For example, the first client device 110 can share GPS information of the first client device 110 when an option opting into receiving exposure notifications is selected on the first client device 110. The cough detection platform 150 determines that the GPS information of the first client device 110 falls within the first ellipsoid or circle. The cough detection platform 150 obtains the weight of the illness prediction for the first ellipsoid or circle, adjusts the weighted illness prediction by the weight associated with the first ellipsoid or circle and compares the adjusted weighted illness prediction to a specified threshold. For example, the weighted illness prediction may indicate that the cough is associated with a 60% likelihood of infection and the first ellipsoid or circle is associated with a 90% weight. In such cases, the adjusted weighted illness prediction is 54% likelihood of infection exposure. In response to determining that the adjusted weighted illness prediction exceeds the threshold (e.g., the adjusted weighted illness prediction exceeds 40% likelihood of infection exposure), the cough detection platform 150 transmits an exposure notification to the first client device 110.

In another example, the cough detection platform 150 determines that a second client device 110 was located within a region covered by the second ellipsoid or circle when the utterance that includes the cough was received. For example, the second client device 110 can share GPS information of the second client device 110 when an option opting into receiving exposure notifications is selected on the second client device 110. The cough detection platform 150 determines that the GPS information of the second client device 110 falls within the second ellipsoid or circle. The cough detection platform 150 obtains the weight of the illness prediction for the second ellipsoid or circle, adjusts the weighted illness prediction by the weight associated with the second ellipsoid or circle and compares the adjusted weighted illness prediction to a specified threshold. For example, the weighted illness prediction may indicate that the cough is associated with a 60% likelihood of infection and the second ellipsoid or circle is associated with a 60% weight. In such cases, the adjusted weighted illness prediction is 21% likelihood of infection exposure. In response to determining that the adjusted weighted illness prediction fails to exceed the threshold (e.g., the adjusted weighted illness prediction fails to exceed 40% likelihood of infection exposure), the cough detection platform 150 does not transmit (prevents transmitting) an exposure notification to the second client device 110. In this way, depending on where different client devices 110 are detected to be relative to the microphone that detected an utterance comprising a cough in a public space, the cough detection platform 150 selectively transmits exposure notifications to the respective client devices 110.

In another example, the cough detection platform 150 determines that a third client device 110 has entered the region covered by the first ellipsoid or circle after a given period of time from when the utterance that includes the cough was received. Namely, the third client device 110 enters the first ellipsoid or circle after the ellipsoid or circle has been reduced in size because of the passage of time. In such cases, the cough detection platform 150 obtains the weight of the illness prediction for the first ellipsoid or circle with the reduced size, adjusts the weighted illness prediction by the weight associated with the first ellipsoid or circle and compares the adjusted weighted illness prediction to the specified threshold. In response to determining that the adjusted weighted illness prediction exceeds the threshold, the cough detection platform 150 transmits an exposure notification to the third client device 110 that entered the region covered by the first ellipsoid or circle after the given period of time from when the utterance that includes the cough was received.

In some embodiments, the cough detection platform 150 is trained to detect intoxication or illness. For example, the cough detection platform 150 can receive a request from the client device 110 to re-fill a prescription. In one example, the request to re-fill the prescription can be made via an IVR system, in which case a sound clip of the user's voice and/or cough can be captured during the phone call with the user. In another example, the request to re-fill the prescription can be made via an application without placing a phone call, in which case the user is instructed to record a sound clip of the user's voice and/or cough. The cough detection platform 150 can store a collection of the captured voices and/or coughs in a profile for the user. The cough detection platform 150 can analyze changes in the voice and/or cough over time as each prescription is re-filled. In some cases, the cough detection platform 150 processes the changes to the voice and/or cough with a machine learning model to determine whether such changes and/or cough are associated with or correspond with a certain likelihood of intoxication or addiction. In response to determining that the changes and/or cough have a certain likelihood or probability of intoxication or addiction (e.g., there is more than a 60% likelihood of intoxication or addiction as output by the machine learning model), the cough detection platform 150 can delay filling the requested prescription and/or can send a notification with a referral to the healthcare provider devices 120. A user of the healthcare provider devices 120 can access the referral and medical records (e.g., medical information 230) of the requesting user and can make contact with the user to treat the possible condition.

The cough detection system 150 can develop a three-dimensional display view on an electronic screen image including the cough source and the individuals who were in the field of the cough utterance. The individuals can be located based on the location of the mobile electronic devices associated with the individuals. The location of the individuals can be dynamically tracked and overlayed at a given time that the utterance is detected after the utterance is determined to be a cough and weighted to be an utterance that is associated with an illness. The map on the display view can be made in real-time.

The cough detection system 150 can also employ a plurality of HIPAA compliant access rules that control at least the hierarchical auditability, the tracking, the user, the display, and the database record access. The rules can also operate to de-identify user identifying information to process the data to determine when the user is around a cough that is weighted to be an illness.

Figure 2:
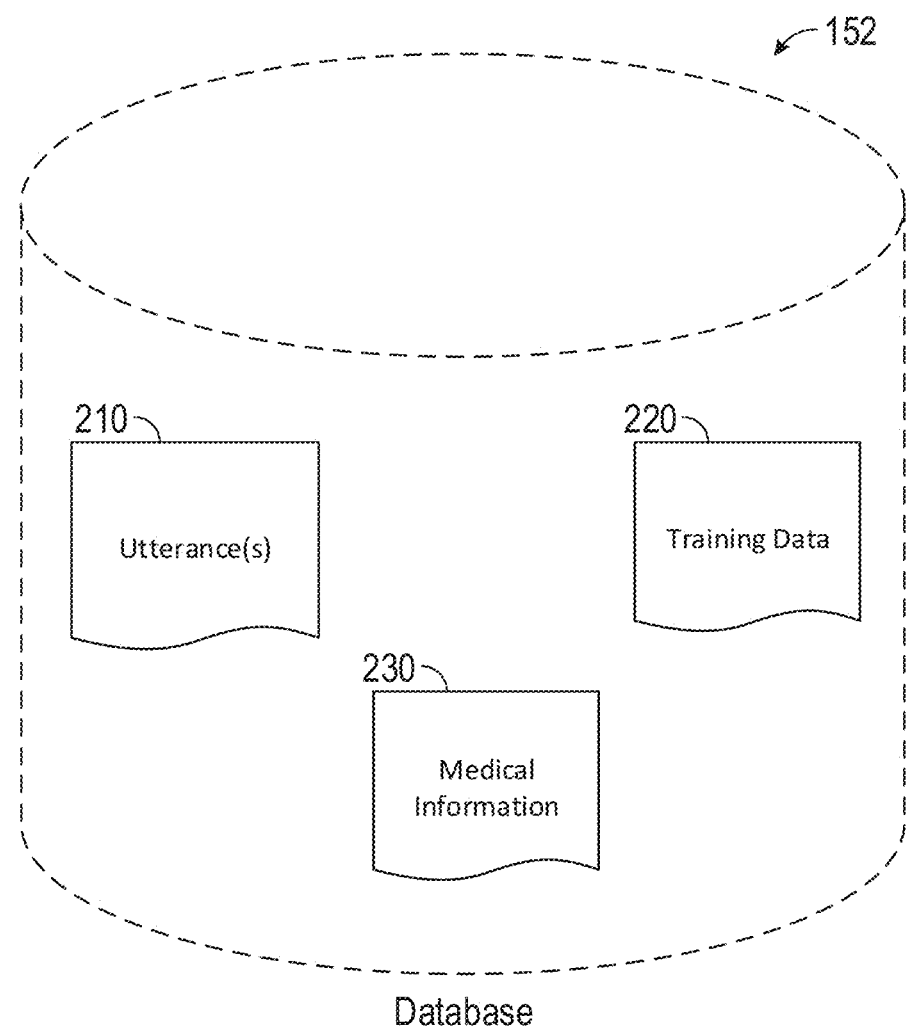
FIG. 2 is an example database that may be deployed within the system of FIG. 1, according to some embodiments.

FIG. 2 is an example database 152 that may be deployed within the system of FIG. 1, according to some embodiments. The database 152 includes stored utterances 210, medical information 230, and training data 220. The utterances 210 can be generated by the utterance processing system 154. For example, after the utterance processing system 154 receives a given utterance (e.g., from a microphone installed in a public space and/or from one or more client devices 110), the utterance processing system 154 processes the utterances to detect a cough and obtain various information (e.g., environmental and/or medical factors) associated with the utterances. The utterance processing system 154 stores sound clips that include the cough together with or associated with the various information.

The medical information 230 stores various medical related information (e.g., prescriptions, preexisting conditions, referral flags, laboratory results, and so forth) for one or more users of client devices 110. Such medical related information is used by the cough detection platform 150 to adjusts or assign weights to illness predictions generated by the illness prediction system 156 based on utterances that include coughs.

The training data 220 includes utterances that comprise coughs and corresponding ground-truth illnesses associated with such coughs. The training data 220 is generated, in one example, in a process discussed in connection with FIG. 4. The training data 220 is used to train a machine learning model implemented by the illness prediction system 156 to generate illness predictions (or likelihoods that a received cough corresponds to certain illnesses). The training data 220 can also be used to train a machine learning model to predict or generate a likelihood that certain voice changes and/or cough are indicative of intoxication or addiction.

Figure 3:
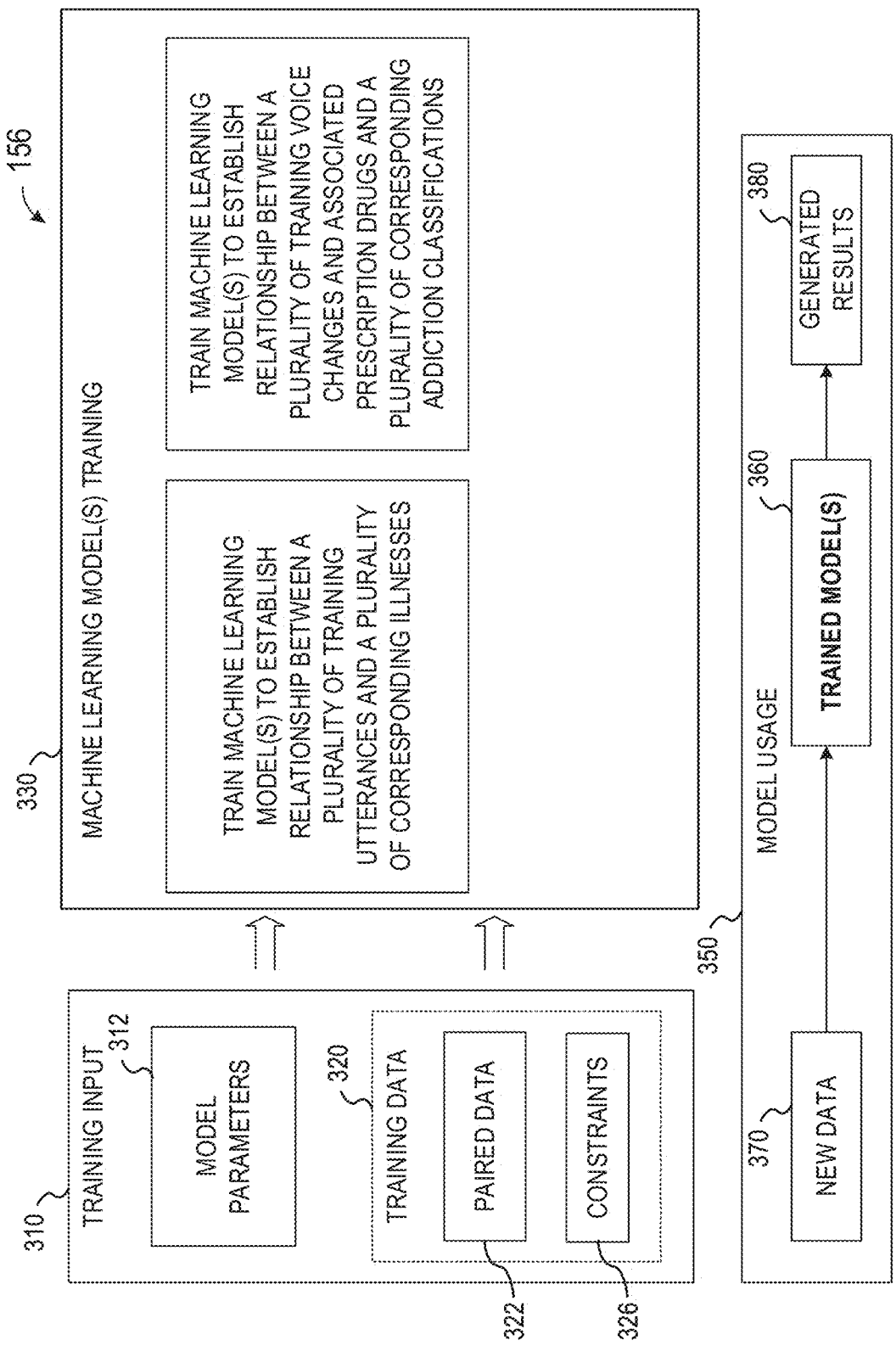
FIG. 3 is a block diagram of an example illness prediction system that may be deployed within the system of FIG. 1, according to some embodiments.

FIG. 3 is a block diagram of an example illness prediction system 156 that may be deployed within the system of FIG. 1, according to some embodiments. Training input 310 includes model parameters 312 and training data 320 (e.g., training data 220 (FIG. 2)) which may include paired training data sets 322 (e.g., input-output training pairs) and constraints 326. Model parameters 312 stores or provides the parameters or coefficients of corresponding ones of machine learning models. During training, these parameters 312 are adapted based on the input-output training pairs of the training data sets 322. After the parameters 312 are adapted (after training), the parameters are used by trained models 360 to implement the trained machine learning models on a new set of data 370.

Training data 320 includes constraints 326 which may define the constraints of a given illness. The paired training data sets 322 may include sets of input-output pairs, such as a pairs of a plurality of training coughs and corresponding training illnesses. The paired training data sets 322 may also include sets of input-output pairs, such as a pairs of a plurality of training coughs and/or voice changes and prescription drugs (e.g., opioids) and corresponding training intoxications and/or addictions. Some components of training input 310 may be stored separately at a different off-site facility or facilities than other components.

Machine learning model(s) training 330 trains one or more machine learning techniques based on the sets of input-output pairs of paired training data sets 322. For example, the model training 330 may train the machine learning (ML) model parameters 312 by minimizing a loss function based on one or more ground-truth illnesses corresponding to coughs. The ML model can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Particularly, the ML model can be applied to a training cough utterance (or features of the training cough utterance) to estimate or generate a prediction with a certain level of likelihood or probability of corresponding to a particular illness or illnesses. In some implementations, a derivative of a loss function is computed based on a comparison of the estimated illness prediction (the likelihood or probability of the corresponding illness or illnesses) and the ground truth illness associated with the training cough utterance and parameters of the ML model are updated based on the computed derivative of the loss function.

As another example, the model training 330 may train the machine learning (ML) model parameters 312 by minimizing a loss function based on one or more ground-truth intoxications or addictions corresponding to voice changes and/or coughs. Particularly, the ML model can be applied to a training cough utterance and/or voice change (or features of the training cough utterance and/or voice change) to estimate or generate a prediction with a certain level of likelihood or probability of corresponding to a particular intoxication or addiction. In some implementations, a derivative of a loss function is computed based on a comparison of the estimated intoxication or addiction prediction (the likelihood or probability of the corresponding intoxication or addiction) and the ground truth intoxication or addiction associated with the training utterance and/or voice change and parameters of the ML model are updated based on the computed derivative of the loss function.

In one example, the ML model receives a training cough together with additional information (e.g., whether the cough corresponds to someone wearing a mask, a spectral density of the cough, an intensity of the cough, medical information associated with the cough, such as whether the cough was received from someone with a preexisting condition, and so forth). The ML model generates a feature vector based on the cough and the additional information and generates a prediction of the illness based on the feature vector. The prediction of the illness is compared with the ground truth indication of whether an illness is present and parameters of the ML model are updated based on the comparison. In this way, the ML model can more accurately generate predictions not only based on the cough alone but also based on additional information associated with the cough (e.g., preexisting conditions, such as asthma, lung cancer, COPD, allergies, presence of a mask, spectral density, and so forth). In some cases, this additional information is used to apply a weight to a prediction made by the ML model based only on an utterance that includes a cough or based only on the utterance that includes the cough and some but not all of the additional information.

The result of minimizing the loss function for multiple sets of training data trains, adapts, or optimizes the model parameters 312 of the corresponding ML models. In this way, the ML model is trained to establish a relationship between a plurality of training utterances comprising coughs and/or voice changes and a corresponding illness prediction, intoxication or addiction prediction.

The ML model is trained in one implementation according to supervised learning techniques to estimate illnesses from training coughs. In such cases, to train the ML model, a plurality of training coughs are retrieved together with their corresponding training illnesses. For example, the training coughs are retrieved from training data 220 stored in database 152 (FIG. 2). The ML model is applied to a first batch of training coughs to estimate a given set of illnesses or probabilities or likelihoods of corresponding to each illness in a set of illnesses. The batch of the training coughs can be used to train the ML model with the same parameters of the ML model and may range from one training cough to all of the training coughs. The estimated or predicted illnesses are compared with the ground-truth illnesses corresponding to the coughs to compute a loss based on a loss function and a gradient or derivative of the loss function with the applied losses is computed. Based on the gradient or derivative of the loss function, updated parameters for the ML model are computed. The ML model is then applied with the updated parameters to a second batch of training coughs to again estimate a given set of illness predictions and apply the illness predictions to a loss function to compute loss based on the ground-truth illnesses associated with the coughs. Parameters of the ML model are again updated and iterations of this training process continue for a specified number of iterations or epochs or until a given convergence criteria has been met.

After the machine learning model is trained, new data 370, including one or more utterances that include a cough and/or voice changes and additional information (e.g., preexisting conditions, such as asthma, lung cancer, COPD, allergies, presence of a mask, spectral density, and so forth), may be received. The trained machine learning technique may be applied to the new data 370 to generate results 380 including a prediction of an illness (with a certain level of likelihood or probability) and/or a prediction of intoxication or addition (with a certain level of likelihood or probability).

Figure 4:
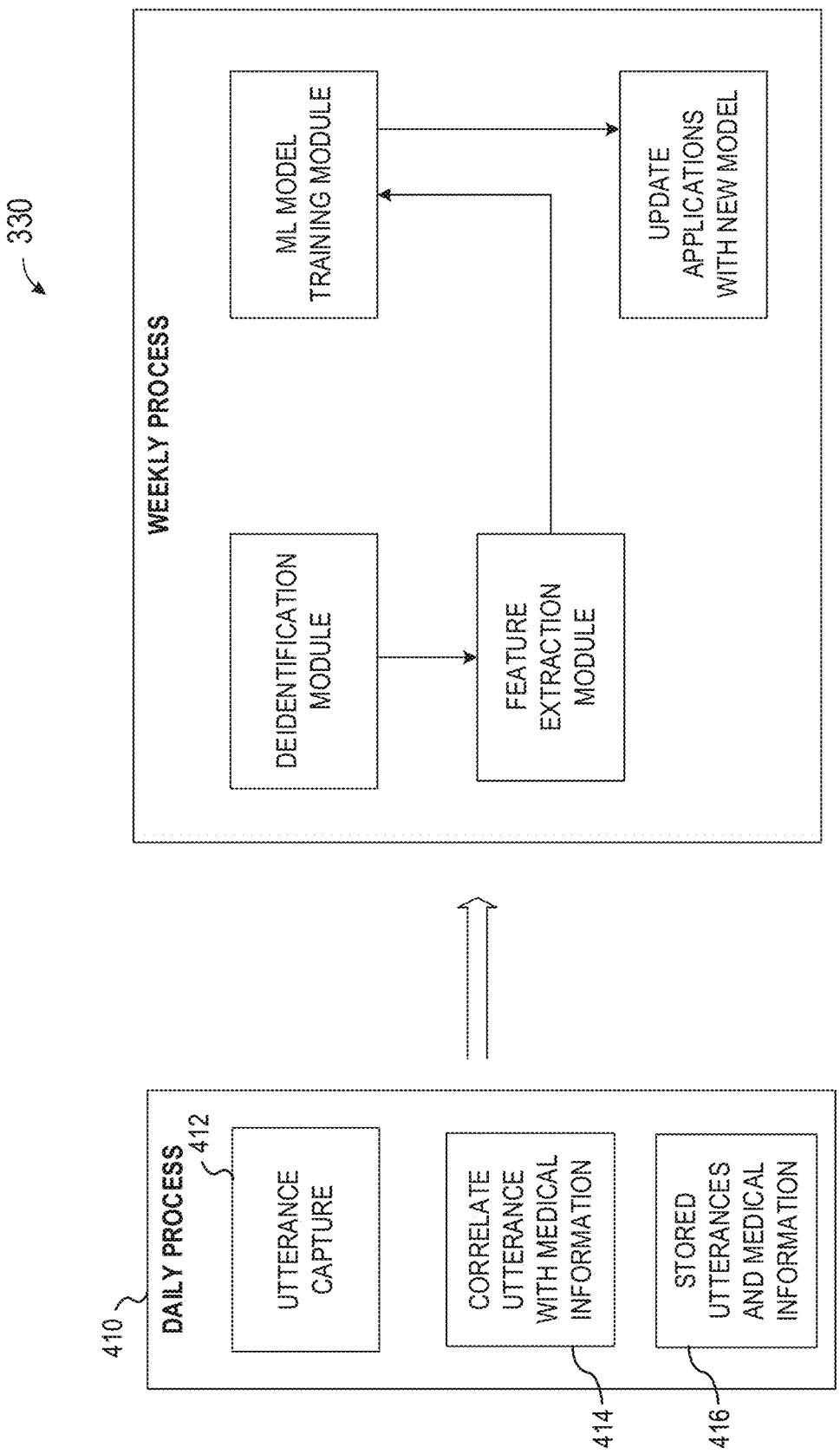
FIG. 4 is an example training system for the illness prediction system, according to some embodiments.

FIG. 4 is an example training system for the illness prediction system, according to some embodiments. In some implementations, the illness prediction system 156 can generate training data 220 daily and can update the ML model weekly. For example, the illness prediction system 156 can communicate with a volunteer through a client device 110 to capture an utterance 412. The volunteer can be instructed to record an utterance that includes a cough several times a day, such as by prompting the volunteer periodically throughout the day. By recording utterances for volunteers multiple times a day and over the course of many weeks, voice changes for specific volunteers can also be determined and collected. Such voice changes can be used to train the ML to detect or predict intoxications or addictions when the medical information associated with the volunteers indicates a diagnosis of intoxication or addiction. The volunteer may be someone who has already been diagnosed with the illness or someone who is at a high risk of being infected by the illness. In some examples, the volunteer may be a user of a IVR system hosted by the cough detection platform 150. In such cases, the utterance is collected passively in response to detecting a cough during a phone call with the volunteer. Medical information associated with the volunteer is accessed by the cough detection platform 150 to associate various information (e.g., indicating preexisting conditions and diagnosis with an illness) with the cough that is passively collected.

The captured utterance is correlated with medical information 414 by the illness prediction system 156. Specifically, the illness prediction system 156 obtains various information about the volunteer including preexisting conditions, such as asthma, lung cancer, COPD, allergies, presence of a mask, spectral density, and so forth. The illness prediction system 156 generates a sound clip that includes the cough and stores that sound clip together with the various information about the volunteer as stored utterances and medical information 416. This process can be repeated multiple times during a day and can be performed for multiple volunteers with their respective client devices 110.

The stored utterances and medical information 416 is provided to the training module of the illness prediction system 156 to perform a weekly training process 330. The weekly training process 330 obtains the stored utterances and medical information 416 and applies noise and a deidentification technique to the data using a deidentification module. This privatizes the data and prevents any sensitive information from being included in the data used to train the ML models. The privatized and deidentified data is provided to a feature extraction module. The feature extraction module generates a feature vector that represents the utterance that includes the cough and that includes some or all of the various medical and/or environmental information associated with the volunteer (e.g., preexisting conditions, such as asthma, lung cancer, COPD, allergies, presence of a mask, spectral density, and so forth). The various medical information can also provide the ground-truth information about a positive result that the individual who provided the utterance (with the cough and/or voice change) has been diagnosed with the illness, intoxication or addiction. This feature vector is provided to the ML model training module which implements the process discussed above with respect to machine learning model training 330 (FIG. 3). Once the ML model has been updated on a weekly basis, the applications that use the ML model to generate the illness predictions and/or intoxication or addiction predictions are updated with the new ML model parameters.

Figure 5:
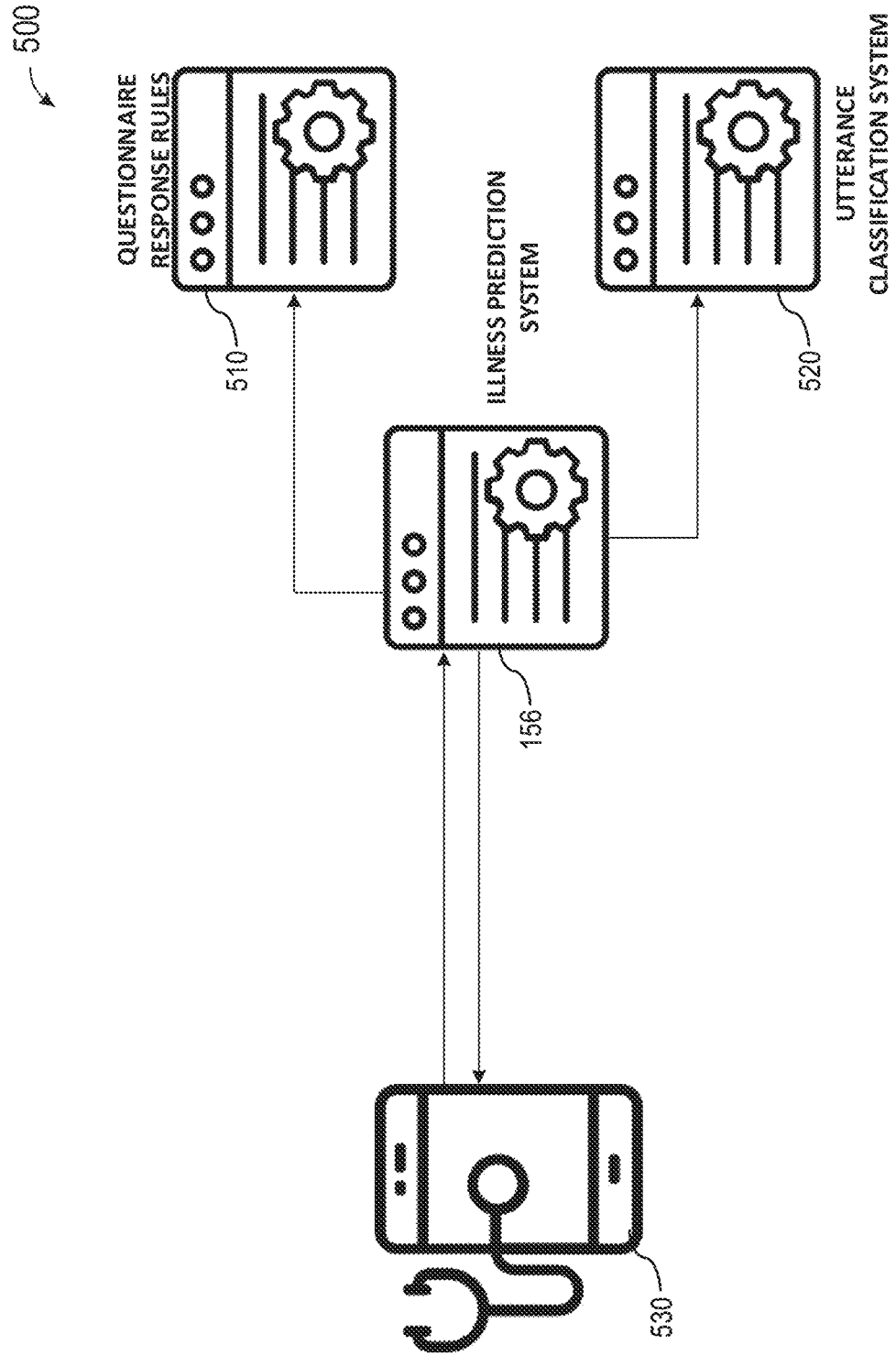
FIG. 5 illustrates example operations of the cough detection system, according to example embodiments.

FIG. 5 illustrates example operations 500 of the cough detection system 100, according to example embodiments. Specifically, a user can use a client device 530 (e.g., the client device 110) to complete an illness questionnaire, survey or attestation. For example, the client device 530 can present a questionnaire 600 (FIG. 6) to the user. The questionnaire 600 can be used to access a public space, school or work. The questionnaire 600 includes a series of medical or illness related questions 610 and 630 along with the current date 620. The illness related questions 610 and 630 can ask the user whether the user has recently experienced health related symptoms like fatigue or fever (e.g., in the past 24 hours). Positive responses to such questions can increase the likelihood that the user is infected with the illness. The questions can also ask the user if the user tested positive for the illness or infection in the past week or other time interval. A positive response to this question may indicate a high likelihood that the user is still contagious and infected by the illness.

The questionnaire 600 can include a request to record a cough 640. As part of completing the questionnaire 600 to obtain access to the public space, school or work, the user can select a record cough option 642. In response, the client device 530 asks the user to cough while a 1 or 2 second sound clip is recorded as an utterance. The client device 530 provides the recorded sound clip along with the responses to the questionnaire 600 to the illness prediction system 156.

The illness prediction system 156 processes the responses to the questionnaire 600 and the recorded sound clip to generate a likelihood or probability that the user is currently contagious with or infected by the illness. Specifically, the illness prediction system 156 provides the sound clip with the cough to the utterance classification system 520. The utterance classification system 520 implements a classifier or machine learning model (e.g., a neural network), such as the ML model discussed in connection with FIG. 3, that is trained to predict an illness based on the sound clip that includes a cough. Specifically, the utterance classification system 520 can generate features based on the sound clip. The utterance classification system 520 predicts or classifies the features of the sound clip with one or more illnesses. In an embodiment, the utterance classification system 520 provides a set of illnesses with their likelihoods or probabilities of matching the cough in the sound clip. In some cases, the utterance classification system 520 determines that the features of the sound clip are not indicative of an illness and, in such cases, outputs an illness prediction indicating that the cough does not match any known illness.

The output of the illness prediction system 156 that includes the illness prediction is then weighted based on the responses to the questionnaire 600. Specifically, the responses to the questionnaire 600 are processed by questionnaire response rules 510 to assign a weight to the total responses. For example, if two or more responses in the questionnaire 600 were indicative of a recent infection or high likelihood of infection, a first weight can be computed and selected. If only one of the responses was indicative of a recent infection or high likelihood of infection, a second weight smaller than the first weight can be computed and selected. The illness prediction system 156 obtains the likelihood of illness or illness prediction from the utterance classification system 520 and multiplies or adjusts the likelihood or the illness prediction based on the weight computed by the questionnaire response rules 510. For example, the illness prediction may indicate a 60% likelihood of infection and the weight may be a first value that increases the likelihood by a certain degree to 70%. The illness prediction system 156 compares the weighted likelihood of infection or the weighted illness prediction with a specified threshold.

In some embodiments, if the weighted illness prediction exceeds a specified threshold (e.g., the weighted predicted illness probability is greater than 60%), the illness prediction system 156 generates an alert to a user of the client device 530 indicating that the utterance that includes the cough together with the responses to the questionnaire 600 is likely indicative of an illness (e.g., COVID-19). The alert can instruct the user to obtain a test kit or visit a testing site to verify whether the user actually has been infected by the illness. The results of the test can be received by the cough detection platform 150 and used to update a patient record for the user and/or to update the parameters of the trained illness prediction system 156. In some cases, the alert can be used to inform the user that the user is not authorized to enter or access a given public space due to the possible infection.

Figure 7:
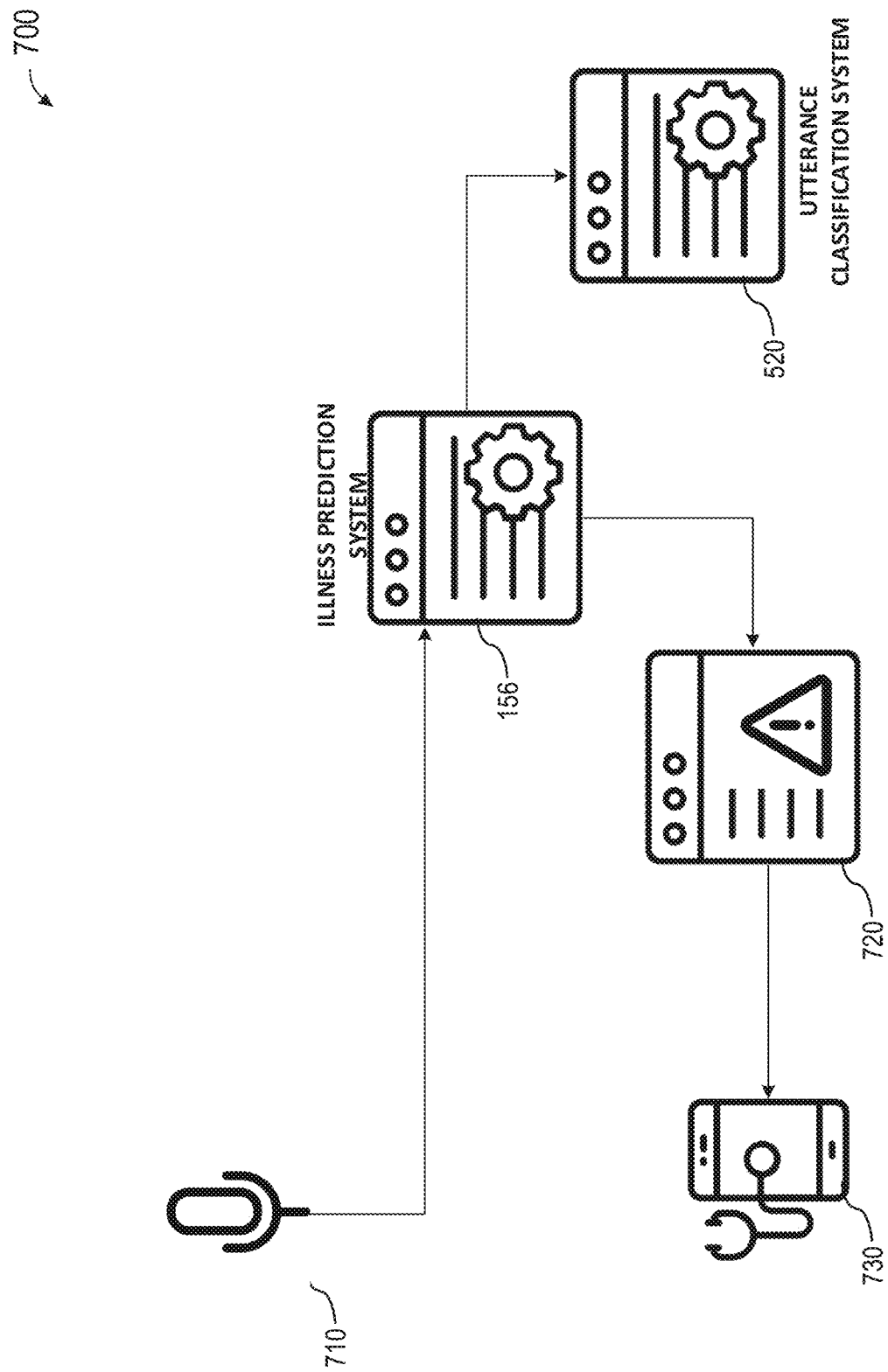
FIG. 7 illustrates example operations of the cough detection system, according to example embodiments.

FIG. 7 illustrates example operations 700 of the cough detection system 100, according to example embodiments. For example, the illness prediction system 156 determines that the utterance was received from a microphone 710 installed in a public space (e.g., a park or a conference room). The illness prediction system 156 provides the utterance that includes the cough together with additional information (e.g., whether the microphone 710 is indoors or outdoors, a current measure of humidity, whether a mask was worn by the user from whom the utterance was received, and various other environmental factors) to the utterance classification system 520. The utterance classification system 520 predicts or classifies the features of the sound clip that includes the cough and the additional information with one or more illnesses. For example, the utterance classification system 520 provides a set of illnesses with their likelihoods or probabilities of matching the cough in the sound clip and based on the additional information. In some cases, the utterance classification system 520 determines that the features of the sound clip are not indicative of an illness and, in such cases, outputs an illness prediction indicating that the cough does not match any known illness. In some cases, the utterance classification system 520 classifies the cough as matching a given illness with a certain level of likelihood or probability and the classification is then weighted by the illness prediction system 156 based on the additional information. For example, if the cough was received outdoors, a low weight is assigned to a positive classification of an illness provided by the utterance classification system 520. As another example, if the utterance was received indoors with a high level of humidity, a higher weight is assigned to the positive classification of the illness.

Figure 8:
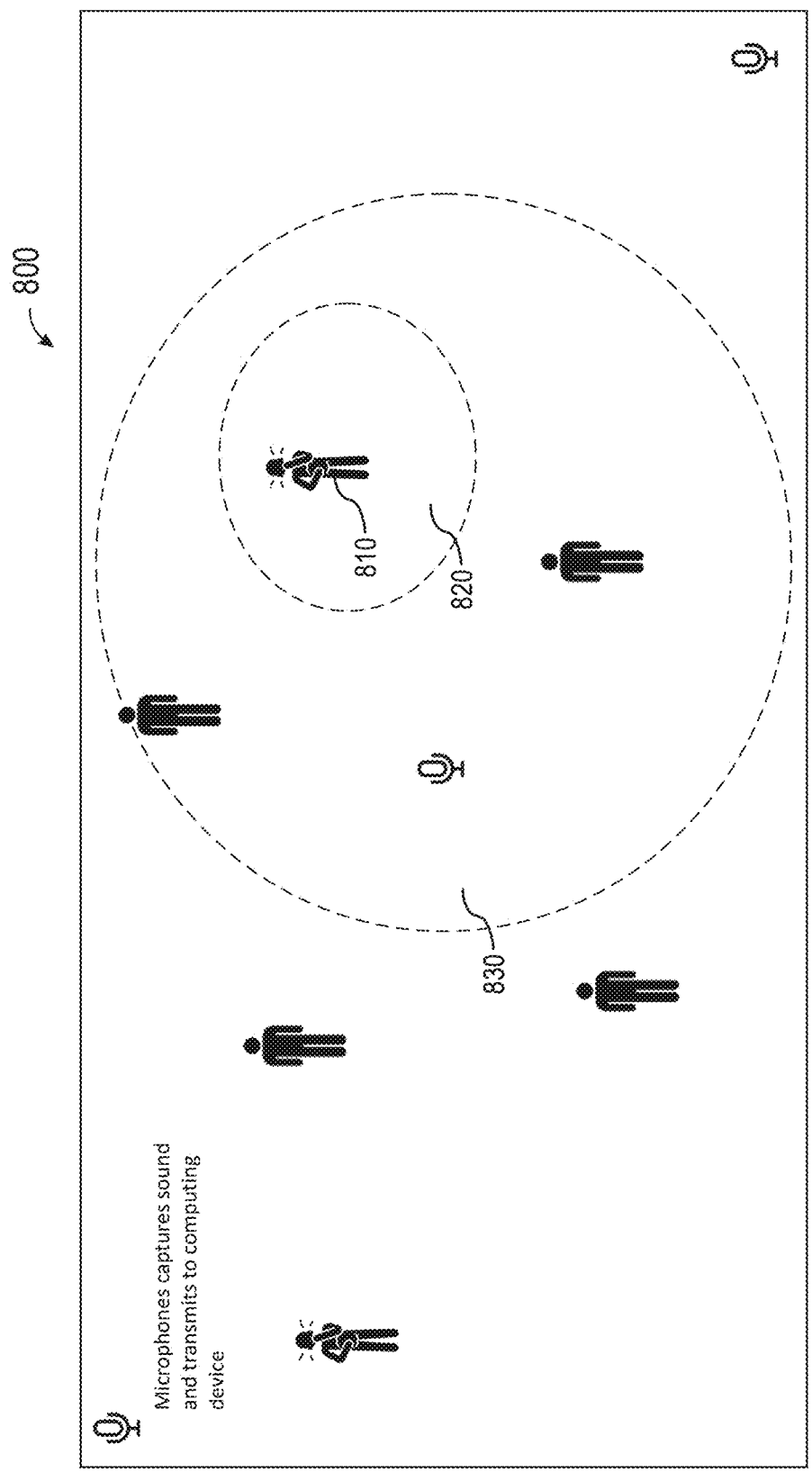
FIG. 8 is an example alert system that can be deployed within the cough detection system, according to example embodiments.

In response to determining that the weighted classification of the illness prediction exceeds a threshold, the illness prediction system 156 identifies a list of users of client devices 110 that opted in or selected an option to receive illness exposure notifications. The illness prediction system 156 applies one or more environmental factors associated with an area 800 that includes the microphone 710 to generate a list of infection regions referred to as ellipsoids or circles 820 and 830 (FIG. 8). Each infection region is associated with a different likelihood of infection.

For example, the illness prediction system 156 generates a first ellipsoid or circle 820 around the user 810 from whom the microphone received the utterance that included the cough. To verify the location and identify of the user 810 from whom the utterance was detected, the illness prediction system 156 can send an exposure alert 1000 (FIG. 10) to a list of users around the region from which the microphone 710 received the utterance. The exposure alert 1000 can ask the users to indicate whether they just recently coughed (e.g., in the past 5 minutes). If a user selects the no option 1020, the illness prediction system 156 excludes that user from the determination of the user from whom the utterance with the cough was received. If the user selects the yes option 1010, the illness prediction system 156 can identify the location of the user and can generate the list of infection regions based on that user's location. The illness prediction system 156 can also determine that the cough was determined to be classified as corresponding to an illness. In such cases, the illness prediction system 156 can present a prompt or alert to the user who selected the yes option 1010 indicating to the user that the user's cough is associated with an illness and recommend to the user to get tested for the illness or quarantine for a period of time.

The first ellipsoid or circle 820 can include a first diameter or be of a first size based on its proximity to the user 810. The illness prediction system 156 can adjust the diameter or first size based on whether the additional information associated with the utterance indicates that the utterance was received indoors or outdoors. The diameter or first size of the ellipsoid or circle 820 can dynamically be shrunk or reduced in size over time. Namely, at a first point in time, the diameter or first size of the ellipsoid or circle 820 can be a first amount and at a later second point in time (e.g., 10 minutes later), the diameter or first size of the ellipsoid or circle 820 can be reduced to a second size. In some embodiments, the diameter or first size of the circle or ellipsoid can be increased or decreased based on a measure of humidity in the area in which the microphone is installed.

The illness prediction system 156 can generate a second ellipsoid or circle 830 around the first ellipsoid or circle 820. The second ellipsoid or circle 830 can include a second diameter or be of a second size based on its proximity to the user 810. The second diameter or second size of the second ellipsoid or circle 830 can be maintained to be greater than the first diameter or first size of the first ellipsoid or circle. The illness prediction system 156 can adjust the diameter or second size of the second ellipsoid or circle in a similar manner as the first ellipsoid or circle 820 (e.g., based on passage of time, based on whether the additional information associated with the utterance indicates that the utterance was received indoors or outdoors, and/or based on whether the additional information associated with the utterance indicates that the utterance was received from a user wearing a mask or not).

The illness prediction system 156 associates different weights for the illness prediction with each region encapsulated or included within the first/second ellipsoids or circles 820 and 830. In an example, the cough illness prediction system 156 determines that a first client device 730 was located within a region covered by the first ellipsoid or circle 820 when the utterance that includes the cough was received. For example, the first client device 730 can share GPS information when an option opting into receiving exposure notifications is selected on the first client device 730. The illness prediction system 156 determines that the GPS information of the first client device 730 falls within the first ellipsoid or circle 820. The illness prediction system 156 obtains the weight of the illness prediction for the first ellipsoid or circle 820, adjusts the weighted illness prediction by the weight associated with the first ellipsoid or circle 820 and compares the adjusted weighted illness prediction to a specified threshold. In response to determining that the adjusted weighted illness prediction exceeds the threshold (e.g., the adjusted weighted illness prediction exceeds 40% likelihood of infection exposure), the illness prediction system 156 transmits an exposure notification 720 to the first client device 730.

Figure 9:
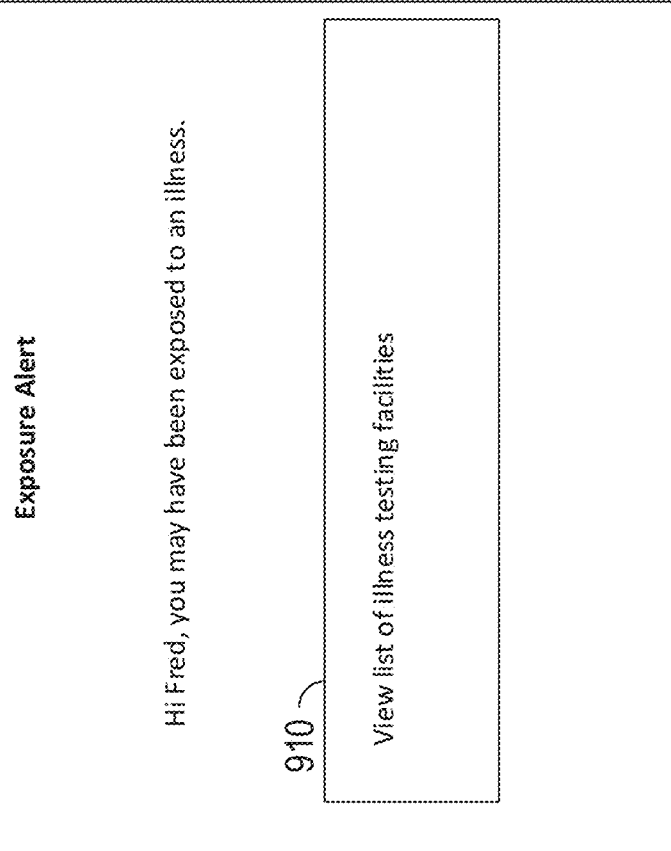
FIGS. 9 and 10 are example user interfaces of the cough detection system, according to example embodiments.
Figure 10:
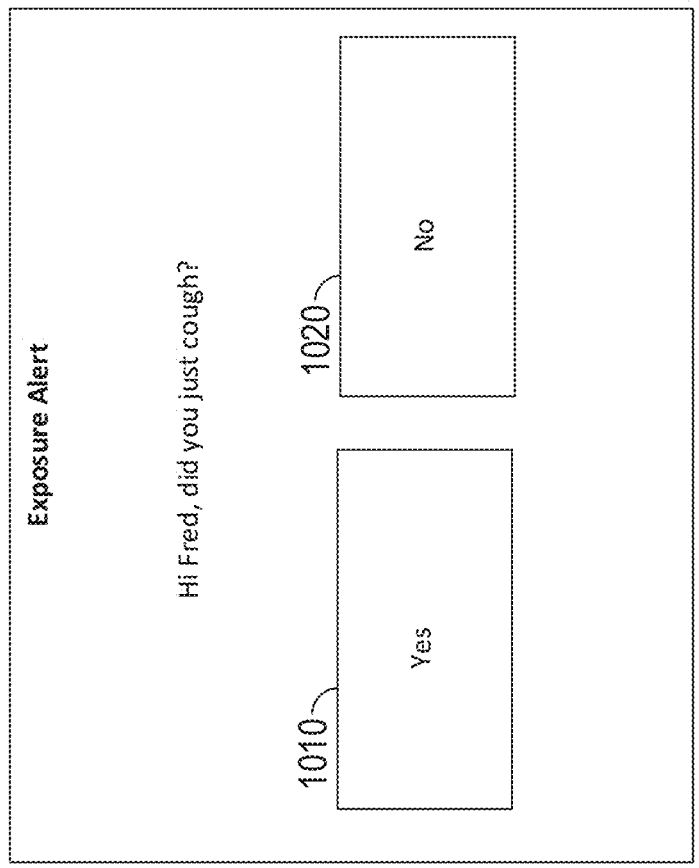

An example exposure notification 900 is shown in FIG. 9. The exposure notification 900 may inform the user of the first client device 730 that the user was in the vicinity of an area where an infected individual was present and recommends to the user to get tested for the illness or quarantine for a given period of time. The user can select an option 910 from the alert to order or schedule a test for the illness.

In another example, the illness prediction system 156 determines that a second client device 730 was located within a region covered by the second ellipsoid or circle 830 when the utterance that includes the cough was received. The illness prediction system 156 obtains the weight of the illness prediction for the second ellipsoid or circle 830, adjusts the weighted illness prediction by the weight associated with the second ellipsoid or circle 830 and compares the adjusted weighted illness prediction to a specified threshold. In response to determining that the adjusted weighted illness prediction fails to exceed the threshold (e.g., the adjusted weighted illness prediction fails to exceed 40% likelihood of infection exposure), the illness prediction system 156 does not transmit (prevents transmitting) an exposure notification 720 to the second client device 730. In this way, depending on where different client devices 730 are detected to be relative to the microphone that detected an utterance comprising a cough in a public space, the illness prediction system 156 selectively transmits exposure notifications to the respective client devices 730.

Figure 11:
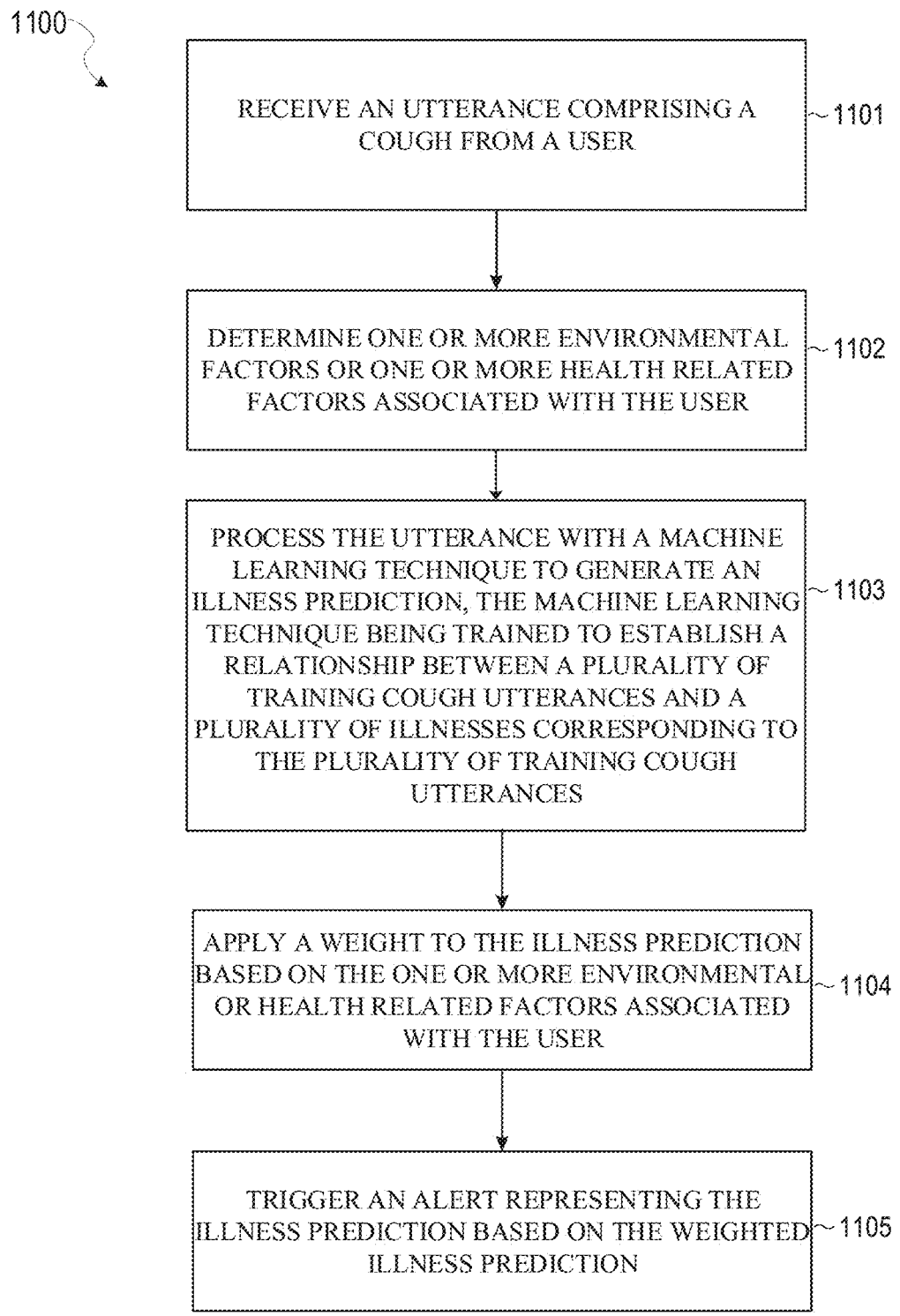
FIG. 11 is a flowchart illustrating example operations of the cough detection system, according to example embodiments.

FIG. 11 is a flowchart illustrating example operations of the visually accessible website system in performing process 1100, according to example embodiments. The process 1100 may be embodied in computer-readable instructions for execution by one or more processors such that the operations of the process 1100 may be performed in part or in whole by the functional components of the system 100; accordingly, the process 1100 is described below by way of example with reference thereto. However, in other embodiments, at least some of the operations of the process 1100 may be deployed on various other hardware configurations. Some or all of the operations of process 1100 can be in parallel, out of order, or entirely omitted.

At operation 1101, the system 100 receives an utterance comprising a cough from a user.

At operation 1102, the system 100 determines one or more environmental factors or one or more health related factors associated with the user.

At operation 1103, the system 100 processes the utterance with a machine learning technique to generate an illness prediction. The machine learning technique can be trained to establish a relationship between a plurality of training cough utterances and a plurality of illnesses corresponding to the plurality of training cough utterances.

At operation 1104, the system 100 applies a weight to the illness prediction based on the one or more environmental or health related factors associated with the user.

At operation 1105, the system 100 triggers an alert representing the illness prediction based on the weighted illness prediction.

Figure 12:
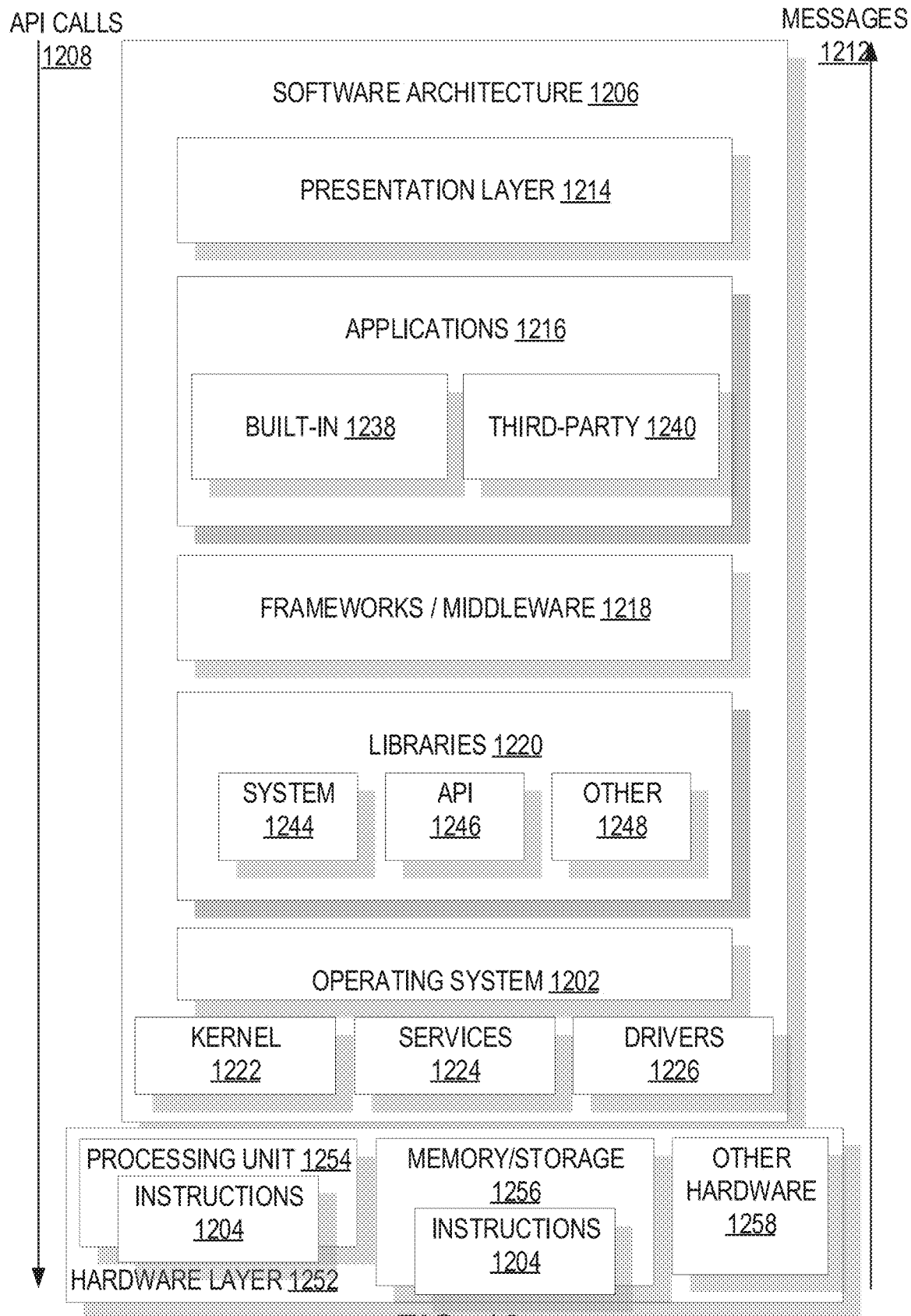
FIG. 12 is a block diagram illustrating an example software architecture, which may be used in conjunction with various hardware architectures herein described.

FIG. 12 is a block diagram illustrating an example software architecture 1206, which may be used in conjunction with various hardware architectures herein described. FIG. 12 is a non-limiting example of a software architecture and it will be appreciated that many other architectures may be implemented to facilitate the functionality described herein. The software architecture 1206 may execute on hardware such as machine 1300 of FIG. 13 that includes, among other things, processors 1304, memory 1314, and input/output (I/O) components 1318. A representative hardware layer 1252 is illustrated and can represent, for example, the machine 1300 of FIG. 13. The representative hardware layer 1252 includes a processing unit 1254 having associated executable instructions 1204. Executable instructions 1204 represent the executable instructions of the software architecture 1206, including implementation of the methods, components, and so forth described herein. The hardware layer 1252 also includes memory and/or storage devices memory/storage 1256, which also have executable instructions 1204. The hardware layer 1252 may also comprise other hardware 1258. The software architecture 1206 may be deployed in any one or more of the components shown in FIG. 1. The software architecture 1206 can be utilized to apply a machine learning technique or model to predict a likelihood of an illness based on a cough and likelihood of exposure to an illness based on vicinity or proximity to another person who recently coughed.

In the example architecture of FIG. 12, the software architecture 1206 may be conceptualized as a stack of layers where each layer provides particular functionality. For example, the software architecture 1206 may include layers such as an operating system 1202, libraries 1220, frameworks/middleware 1218, applications 1216, and a presentation layer 1214. Operationally, the applications 1216 and/or other components within the layers may invoke API calls 1208 through the software stack and receive messages 1212 in response to the API calls 1208. The layers illustrated are representative in nature and not all software architectures have all layers. For example, some mobile or special purpose operating systems may not provide a frameworks/middleware 1218, while others may provide such a layer. Other software architectures may include additional or different layers.

The operating system 1202 may manage hardware resources and provide common services. The operating system 1202 may include, for example, a kernel 1222, services 1224, and drivers 1226. The kernel 1222 may act as an abstraction layer between the hardware and the other software layers. For example, the kernel 1222 may be responsible for memory management, processor management (e.g., scheduling), component management, networking, security settings, and so on. The services 1224 may provide other common services for the other software layers. The drivers 1226 are responsible for controlling or interfacing with the underlying hardware. For instance, the drivers 1226 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1220 provide a common infrastructure that is used by the applications 1216 and/or other components and/or layers. The libraries 1220 provide functionality that allows other software components to perform tasks in an easier fashion than to interface directly with the underlying operating system 1202 functionality (e.g., kernel 1222, services 1224 and/or drivers 1226). The libraries 1220 may include system libraries 1244 (e.g., C standard library) that may provide functions such as memory allocation functions, string manipulation functions, mathematical functions, and the like. In addition, the libraries 1220 may include API libraries 1246 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 1220 may also include a wide variety of other libraries 1248 to provide many other APIs to the applications 1216 and other software components/devices.

The frameworks/middleware 1218 (also sometimes referred to as middleware) provide a higher-level common infrastructure that may be used by the applications 1216 and/or other software components/devices. For example, the frameworks/middleware 1218 may provide various graphic user interface functions, high-level resource management, high-level location services, and so forth. The frameworks/middleware 1218 may provide a broad spectrum of other APIs that may be utilized by the applications 1216 and/or other software components/devices, some of which may be specific to a particular operating system 1202 or platform.

The applications 1216 include built-in applications 1238 and/or third-party applications 1240. Examples of representative built-in applications 1238 may include, but are not limited to, a contacts application, a browser application, a book reader application, a location application, a media application, a messaging application, and/or a game application. Third-party applications 1240 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 1240 may invoke the API calls 1208 provided by the mobile operating system (such as operating system 1202) to facilitate functionality described herein.

The applications 1216 may use built-in operating system functions (e.g., kernel 1222, services 1224, and/or drivers 1226), libraries 1220, and frameworks/middleware 1218 to create UIs to interact with users of the system. Alternatively, or additionally, in some systems, interactions with a user may occur through a presentation layer, such as presentation layer 1214. In these systems, the application/component "logic" can be separated from the aspects of the application/component that interact with a user.

Figure 13:
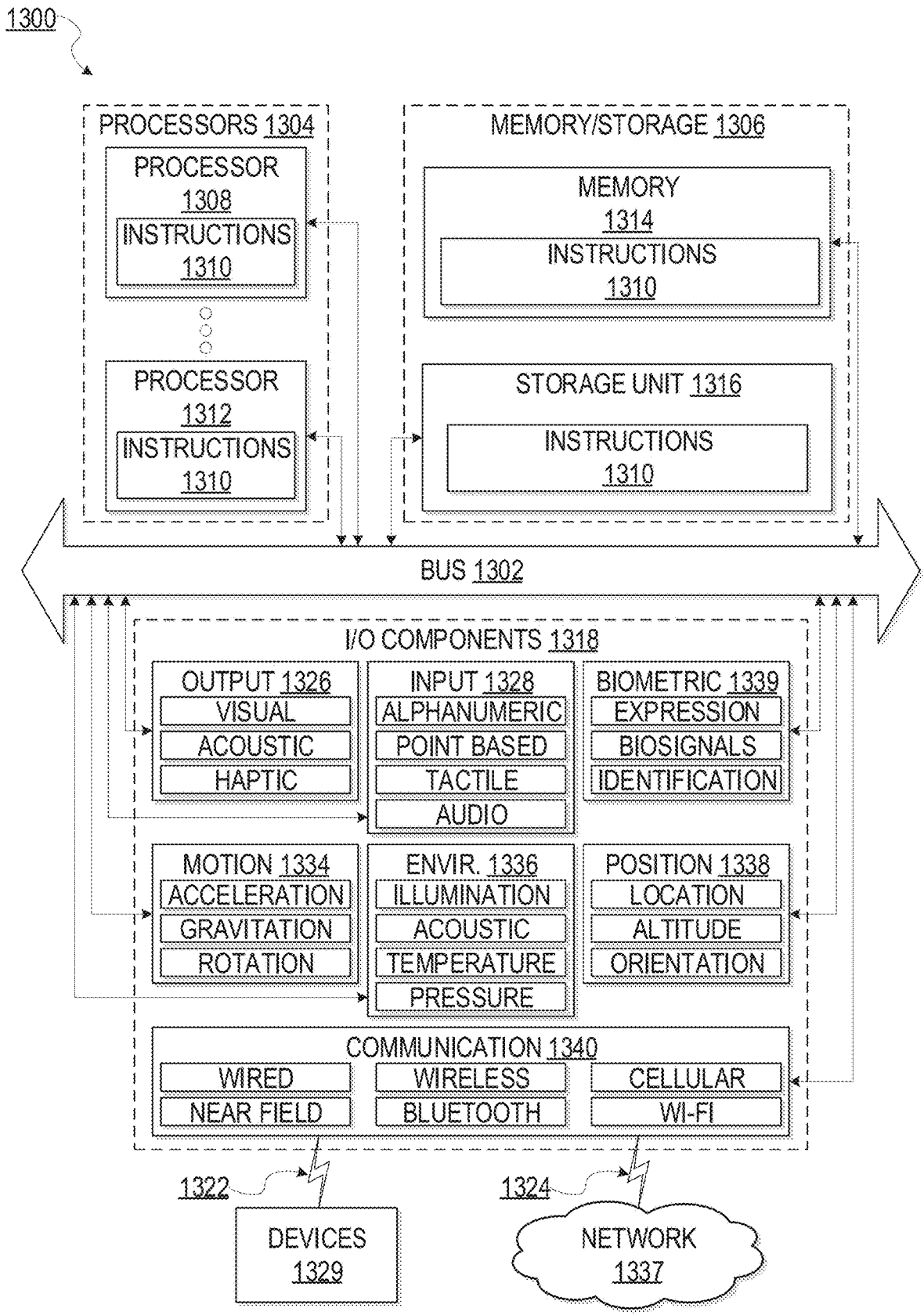
FIG. 13 is a block diagram illustrating components of a machine, according to some example embodiments.

FIG. 13 is a block diagram illustrating components of a machine 1300, according to some example embodiments, able to read instructions from a machine-readable medium (e.g., a machine-readable storage medium) and perform any one or more of the methodologies discussed herein. Specifically, FIG. 13 shows a diagrammatic representation of the machine 1300 in the example form of a computer system, within which instructions 1310 (e.g., software, a program, an application, an applet, an app, or other executable code) for causing the machine 1300 to perform any one or more of the methodologies discussed herein may be executed. For example, the instructions 1310 may be executed by the system 100 to process an utterance that includes a cough with a trained machine learning model to predict a likelihood of an illness based on a cough and likelihood of exposure to an illness based on vicinity or proximity to another person who recently coughed.

As such, the instructions 1310 may be used to implement devices or components described herein. The instructions 1310 transform the general, non-programmed machine 1300 into a particular machine 1300 programmed to carry out the described and illustrated functions in the manner described. In alternative embodiments, the machine 1300 operates as a standalone device or may be coupled (e.g., networked) to other machines. In a networked deployment, the machine 1300 may operate in the capacity of a server machine or a client machine in a server-client network environment, or as a peer machine in a peer-to-peer (or distributed) network environment. The machine 1300 may comprise, but not be limited to a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1310, sequentially or otherwise, that specify actions to be taken by machine 1300. Further, while only a single machine 1300 is illustrated, the term "machine" shall also be taken to include a collection of machines that individually or jointly execute the instructions 1310 to perform any one or more of the methodologies discussed herein.

The machine 1300 may include processors 1304, memory/storage 1306, and I/O components 1318, which may be configured to communicate with each other such as via a bus 1302. In an example embodiment, the processors 1304 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 1308 and a processor 1312 that may execute the instructions 1310. The term "processor" is intended to include multi-core processors 1304 that may comprise two or more independent processors (sometimes referred to as "cores") that may execute instructions contemporaneously. Although FIG. 13 shows multiple processors 1304, the machine 1300 may include a single processor with a single core, a single processor with multiple cores (e.g., a multi-core processor), multiple processors with a single core, multiple processors with multiple cores, or any combination thereof.

The memory/storage 1306 may include a memory 1314, such as a main memory, or other memory storage, database 152, and a storage unit 1316, both accessible to the processors 1304 such as via the bus 1302. The storage unit 1316 and memory 1314 store the instructions 1310 embodying any one or more of the methodologies or functions described herein. The instructions 1310 may also reside, completely or partially, within the memory 1314, within the storage unit 1316, within at least one of the processors 1304 (e.g., within the processor's cache memory), or any suitable combination thereof, during execution thereof by the machine 1300. Accordingly, the memory 1314, the storage unit 1316, and the memory of processors 1304 are examples of machine-readable media.

The I/O components 1318 may include a wide variety of components to receive input, provide output, produce output, transmit information, exchange information, capture measurements, and so on, such as devices 132*a-b*, 133*a-b*, and 134*a-b*. The specific I/O components 1318 that are included in a particular machine 1300 will depend on the type of machine. For example, portable machines such as mobile phones will likely include a touch input device or other such input mechanisms, while a headless server machine will likely not include such a touch input device. It will be appreciated that the I/O components 1318 may include many other components that are not shown in FIG. 13. The I/O components 1318 are grouped according to functionality merely for simplifying the following discussion and the grouping is in no way limiting. In various example embodiments, the I/O components 1318 may include output components 1326 and input components 1328. The output components 1326 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1328 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1318 may include biometric components 1339, motion components 1334, environmental components 1336, or position components 1338 among a wide array of other components. For example, the biometric components 1339 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1334 may include acceleration sensor components (e.g., accelerometer), gravitation sensor components, rotation sensor components (e.g., gyroscope), and so forth. The environmental components 1336 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1338 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1318 may include communication components 1340 operable to couple the machine 1300 to a network 1337 or devices 1329 via coupling 1324 and coupling 1322, respectively. For example, the communication components 1340 may include a network interface component or other suitable device to interface with the network 1337. In further examples, communication components 1340 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1329 may be another machine or any of a wide variety of peripheral devices (e.g., a peripheral device coupled via a USB).

Moreover, the communication components 1340 may detect identifiers or include components operable to detect identifiers. For example, the communication components 1340 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1340, such as location via Internet Protocol (IP) geo-location, location via Wi-Fi® signal triangulation, location via detecting a NFC beacon signal that may indicate a particular location, and so forth.

Glossary

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second.

"Online questionnaire" in the context of the present disclosure may refer to an interactive display as shown on an electronic device or a non-paper questionnaire. The interactivity can be a machine-to-machine interface or a human-to-machine interface. An application, which can turn an electronic device into a special purpose, dedicated device, can retrieve data to produce the interactive display, such as queries and layout data.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
   receiving, by one or more processors, an utterance including a cough from a user;
   in response to receiving the utterance, automatically determining, by the one or more processors, a set of environmental factors and a set of health related factors associated with the user, wherein the set of environmental factors includes at least one of: a spectral density associated with the utterance, an intensity of the utterance, an amount of ambient noise present in the utterance, a measure of humidity in an area in which the utterance was captured, an indication of whether a mask was worn by the user when the utterance was captured, or an indication of whether the utterance was captured indoors or outdoors;

in response to determining the set of environmental factors and the set of health related factors, automatically generating, by the one or more processors, a sound clip of the utterance including only the cough;
inputting the sound clip into a machine learning model to generate an illness prediction, wherein the machine learning model is trained to establish a relationship between a plurality of training cough utterances and a plurality of illnesses corresponding to the plurality of training cough utterances;
applying a weight to the illness prediction based on at least one environmental factor of the set of environmental factors or at least one health related factor of the set of health related factors;
triggering an alert representing the illness prediction based on the weighted illness prediction, including:
  adding the alert to a patient record associated with the user,
  storing the patient record in a database, and
  transmitting the alert to a client device associated with the user;
generating a three-dimensional image including a location of the utterance and a set of individuals located proximate the location of the utterance; and
displaying the three-dimensional image on the client device.

2. The method of claim 1, wherein:
the client device includes a microphone,
the utterance is captured by the microphone, and
the client device transmits the utterance to a server to generate the illness prediction.

3. The method of claim 1, further comprising:
pre-processing the utterance; and
detecting a presence of the cough in the utterance.

4. The method of claim 1, wherein the set of health related factors associated with the user includes a pre-existing health condition of the user, a medical history of the user, an indication of whether the user has a fever, or an indication of whether the user experiences fatigue.

5. The method of claim 1, wherein the machine learning model includes a neural network.

6. The method of claim 1, further comprising:
causing display, on the client device associated with the user, a survey including one or more health related questions;
receiving input from the user including responses to the survey, wherein the responses include the set of health related factors; and
causing the client device to capture, during completion of the survey, the sound clip.

7. The method of claim 6, further comprising:
determining that the weighted illness prediction exceeds a specified threshold; and
in response to determining that the weighted illness prediction exceeds the specified threshold, causing the client device to notify the user that the responses and the sound clip are indicative of an illness.

8. The method of claim 1, further comprising:
receiving the utterance from a microphone in a public space; and
applying a plurality of additional weights to the illness prediction, wherein:
  each weight of the plurality of additional weights is associated with a different distance from the location of the utterance,
  a first weight of the plurality of additional weights is applied to the illness prediction in association with a first region that is within a first distance to the location of the utterance to generate a second weighted illness prediction,
  a second weight of the plurality of additional weights is applied to the illness prediction in association with a second region that is within a second distance to the location of the utterance to generate a third weighted illness prediction, and
  the second distance is greater than the first distance.

9. The method of claim 8, further comprising:
identifying a first client device that was within the first region when the utterance was captured;
determining that the second weighted illness prediction exceeds a specified threshold; and
in response to determining that the second weighted illness prediction exceeds the specified threshold, causing the first client device to notify a user of the first client device of a possible exposure to an illness associated with the illness prediction.

10. The method of claim 9, further comprising:
identifying a second client device that was within the second region when the utterance was captured;
determining that the third weighted illness prediction associated with the second region fails to exceed the specified threshold; and
in response to determining that the third weighted illness prediction associated with the second region fails to exceed the specified threshold, preventing the second client device from notifying a user of the second client device of the possible exposure to the illness.

11. The method of claim 8, further comprising:
identifying a first client device that entered the first region after a given period of time has elapsed from when the utterance was captured;
reducing the second weighted illness prediction associated with the first region based on the given period of time;
determining that the reduced second weighted illness prediction associated with the first region exceeds a specified threshold; and
in response to determining that the reduced second weighted illness prediction associated with the first region exceeds the specified threshold, causing the first client device to notify a user of the first client device of a possible exposure to an illness associated with the illness prediction.

12. The method of claim 8, further comprising:
performing a first adjustment to the second and the third weighted illness predictions associated with the first and second regions based on whether the public space is indoors or outdoors; and
performing a second adjustment to the second and the third weighted illness predictions associated with the first and second regions based on whether a mask was worn by the user.

13. The method of claim 8, further comprising receiving input from client devices within the public space opting into receiving possible exposure notifications of an illness associated with the illness prediction.

14. The method of claim 1, further comprising:
receiving a request from the user to conduct a test to detect an infection; and
selecting a testing kit of a plurality of testing kits based on the weighted illness prediction, wherein:
  each testing kit of the plurality of testing kits is associated with a different level of accuracy, and triggering the alert includes transmitting a notification to the client device of the user that identifies the selected testing kit that the user is authorized to use to conduct the test.

15. The method of claim 1, further comprising:
determining that the illness prediction corresponds to a specific type of illness associated with a follow up; and
communicating to a client device of a health care professional an identification of the user and the weighted illness prediction.

16. The method of claim 1, further comprising:
receiving, from the user, a plurality of utterances over a determined time interval;
detecting changes to a voice of the user based on the plurality of utterances;
identifying a prescription associated with the user; and
detecting an addiction based on the changes to the voice of the user and the prescription associated with the user.

17. The method of claim 1, wherein training the machine learning model includes:
obtaining a first batch of training data including a first set of the plurality of training cough utterances and a first set of the corresponding plurality of illnesses;
processing the first set of the plurality of training cough utterances with the machine learning model to generate an estimated illness prediction;
computing a loss based on a deviation between the estimated illness prediction and the corresponding plurality of illnesses; and
updating parameters of the machine learning model based on the computed loss.

18. A system comprising:
one or more processors coupled to a memory including non-transitory computer instructions that, when executed by the one or more processors, perform operations including:
receiving an utterance including a cough from a user;
in response to receiving the utterance, automatically determining a set of environmental factors and a set of health related factors associated with the user, wherein the set of environmental factors includes at least one of: a spectral density associated with the utterance, an intensity of the utterance, an amount of ambient noise present in the utterance, a measure of humidity in an area in which the utterance was captured, an indication of whether a mask was worn by the user when the utterance was captured, or an indication of whether the utterance was captured indoors or outdoors;
in response to determining the set of environmental factors and the set of health related factors, automatically generating a sound clip of the utterance including only the cough;
inputting the sound clip into a machine learning model to generate an illness prediction, wherein the machine learning model is trained to establish a relationship between a plurality of training cough utterances and a plurality of illnesses corresponding to the plurality of training cough utterances;
applying a weight to the illness prediction based on at least one environmental factor of the set of environmental factors or at least one health related factor of the set of health related factors;
triggering an alert representing the illness prediction based on the weighted illness prediction, including:
adding the alert to a patient record associated with the user,
storing the patient record in a database, and
transmitting the alert to a client device associated with the user;
generating a three-dimensional image including a location of the utterance and a set of individuals located proximate the location of the utterance; and
displaying the three-dimensional image on the client device.

19. A non-transitory computer readable medium comprising non-transitory computer-readable instructions for performing operations including:
receiving an utterance including a cough from a user;
in response to receiving the utterance, automatically determining a set of environmental factors and a set of health related factors associated with the user, wherein the set of environmental factors includes at least one of: a spectral density associated with the utterance, an intensity of the utterance, an amount of ambient noise present in the utterance, a measure of humidity in an area in which the utterance was captured, an indication of whether a mask was worn by the user when the utterance was captured, or an indication of whether the utterance was captured indoors or outdoors;
in response to determining the set of environmental factors and the set of health related factors, automatically generating a sound clip of the utterance including only the cough;
inputting the sound clip into a machine learning model to generate an illness prediction, wherein the machine learning model is trained to establish a relationship between a plurality of training cough utterances and a plurality of illnesses corresponding to the plurality of training cough utterances;
applying a weight to the illness prediction based on the at least one environmental factor of the set of environmental factors or at least one health related factor of the set of health related factors;
triggering an alert representing the illness prediction based on the weighted illness prediction, including:
adding the alert to a patient record associated with the user;
storing the patient record in a database; and
transmitting the alert to a client device associated with the user;
generating a three-dimensional image including a location of the utterance and a set of individuals located proximate the location of the utterance; and
displaying the three-dimensional image on the client device.

* * * * *